(12) United States Patent
Bachelet et al.

(10) Patent No.: US 9,765,341 B2
(45) Date of Patent: Sep. 19, 2017

(54) DNA ORIGAMI DEVICES

(75) Inventors: Ido Bachelet, Modi'in (IL); Shawn Douglas, Brookline, MA (US); George Church, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 543 days.

(21) Appl. No.: 13/882,753

(22) PCT Filed: Nov. 4, 2011

(86) PCT No.: PCT/US2011/059352
§ 371 (c)(1),
(2), (4) Date: May 1, 2013

(87) PCT Pub. No.: WO2012/061719
PCT Pub. Date: May 10, 2012

(65) Prior Publication Data
US 2013/0224859 A1    Aug. 29, 2013

Related U.S. Application Data

(60) Provisional application No. 61/410,102, filed on Nov. 4, 2010.

(51) Int. Cl.
*C12N 15/115* (2010.01)
*C12Q 1/68* (2006.01)
*C12N 15/11* (2006.01)
*A61K 48/00* (2006.01)
*C12N 15/87* (2006.01)

(52) U.S. Cl.
CPC ........ *C12N 15/115* (2013.01); *A61K 48/0025* (2013.01); *A61K 48/0091* (2013.01); *C12N 15/111* (2013.01); *C12N 15/87* (2013.01); *C12Q 1/68* (2013.01); *C12N 2310/16* (2013.01); *C12N 2310/3519* (2013.01); *C12N 2310/532* (2013.01); *C12N 2320/32* (2013.01); *C12Q 2525/205* (2013.01)

(58) Field of Classification Search
None
See application file for complete search history.

(56) References Cited

U.S. PATENT DOCUMENTS

| 5,451,503 A * | 9/1995 | Hogan et al. ...... C12N 15/1068 435/6.1 |
| 2006/0068407 A1 | 3/2006 | Rupcich et al. |
| 2007/0117109 A1 | 5/2007 | Rothemund |
| 2008/0293160 A1 * | 11/2008 | Sen et al. ................... 436/501 |

FOREIGN PATENT DOCUMENTS

WO    2007/127020    11/2007

OTHER PUBLICATIONS

Mok et al, Sensors, vol. 8, pp. 7050-7084, published Nov. 7, 2008.*
Niemeyer, Current Op. Chem. Bio, vol. 4, pp. 609-618 (2000).*
Anderson et al., Nature, 459(11):73-76 (2009). "Self-assembly of a nanoscale DNA box with a controllable lid."
Ke et al., Nano Letters, 9(6):2445-2447 (2009). "Scaffolded DNA origami of a DNA tetrahedron molecular container.".

* cited by examiner

*Primary Examiner* — Robert T Crow
(74) *Attorney, Agent, or Firm* — Banner & Witcoff, Ltd.

(57) ABSTRACT

Provided herein are DNA origami devices useful in the targeted delivery of biologically active entities to specific cell populations.

24 Claims, 25 Drawing Sheets

FIG. 2: scaffold sequence (SEQ ID NO: 1)

```
AATGCTACTACTATTAGTAGAATTGATGCCACCTTTTCAGCTCGCGCCCCAAATGAAAATATAGCTAAACAGGTTAT
TGACCATTTGCGAAATGTATCTAATGGTCAAACTAAATCTACTCGTTCGCAGAATTGGGAATCAACTGTTATATGGA
ATGAAACTTCCAGACACCGTACTTTAGTTGCATATTTAAAACATGTTGAGCTACAGCATTATATTCAGCAATTAAGC
TCTAAGCCATCCGCAAAAATGACCTCTTATCAAAAGGAGCAATTAAAGGTACTCTCTAATCCTGACCTGTTGGAGTT
TGCTTCCGGTCTGGTTCGCTTTGAAGCTCGAATTAAAACGCGATATTTGAAGTCTTTCGGGCTTCCTCTTAATCTTT
TTGATGCAATCCGCTTTGCTTCTGACTATAATAGTCAGGGTAAAGACCTGATTTTTGATTTATGGTCATTCTCGTTT
TCTGAACTGTTTAAAGCATTTGAGGGGGATTCAATGAATATTTATGACGATTCCGCAGTATTGGACGCTATCCAGTC
TAAACATTTTACTATTACCCCCTCTGGCAAAACTTCTTTTGCAAAAGCCTCTCGCTATTTTGGTTTTTATCGTCGTC
TGGTAAACGAGGGTTATGATAGTGTTGCTCTTACTATGCCTCGTAATTCCTTTTGGCGTTATGTATCTGCATTAGTT
GAATGTGGTATTCCTAAATCTCAACTGATGAATCTTTCTACCTGTAATAATGTTGTTCCGTTAGTTCGTTTTATTAA
CGTAGATTTTCTTCCCAACGTCCTGACTGGTATAATGAGCCAGTTCTTAAAATCGCATAAGGTAATTCACAATGAT
TAAAGTTGAAATTAAACCATCTCAAGCCCAATTTACTACTCGTTCTGGTGTTTCTCGTCAGGGCAAGCCTTATTCAC
TGAATGAGCAGCTTTGTTACGTTGATTTGGGTAATGAATATCCGGTTCTTGTCAAGATTACTCTTGATGAAGGTCAG
CCAGCCTATGCGCCTGGTCTGTACACCGTTCATCTGTCCTCTTTCAAAGTTGGTCAGTTCGGTTCCCTTATGATTGA
CCGTCTGCGCCTCGTTCCGGCTAAGTAACATGGAGCAGGTCGCGGATTTCGACACAATTTATCAGGCGATGATACAA
ATCTCCGTTGTACTTTGTTTCGCGCTTGGTATAATCGCTGGGGGTCAAAGATGAGTGTTTTAGTGTATTCTTTTGCC
TCTTTCGTTTTAGGTTGGTGCCTTCGTAGTGGCATTACGTATTTTACCCGTTTAATGGAAACTTCCTCATGAAAAAG
TCTTTAGTCCTCAAAGCCTCTGTAGCCCGTTGCTACCCTCGTTCCGATGCTGTCTTTCGCTGCTGAGGGTGACGATCC
CGCAAAAGCGGCCTTTAACTCCCTGCAAGCCTCAGCGACCGAATATCGGTTATGCGTGGGCGATGGTTGTTGTCA
TTGTCGGCGCAACTATCGGTATCAAGCTGTTTAAGAAATTCACCTCGAAAGCAAGCTGATAAACCGATACAATTAAA
GGCTCCTTTTGGAGCCTTTTTTTGGAGATTTTCAACGTGAAAAAATTATTATTCGCAATTCCTTTAGTTGTTCCTT
TCTATTCTCACTCCGCTGAAACTGTTGAAAGTTGTTTAGCAAAATCCCATACAGAAAATTCATTTACTAACGTCTGG
AAAGACGACAAAACTTTAGATCGTTACGCTAACTATGAGGGCTGTCTGTGGAATGCTACAGGCGTTGTAGTTTGTAC
TGGTGACGAAACTCAGTGTTACGGTACATGGGTTCCTATTGGGCTTGCTATCCCTGAAAATGAGGGTGGTGGCTCTG
AGGGTGGCGGTTCTGAGGGTGGCGGTTCTGAGGGTGGCGGTACTAAACCTCCTGAGTACGGTGATACACCTATTCCG
GGCTATACTTATATCAACCCTCTCGACGGCACTTATCCGCCTGGTACTGAGCAAAACCCCGCTAATCCTAATCCTTC
TCTTGAGGAGTCTCAGCCTCTTAATACTTTCATGTTTCAGAATAATAGGTTCCGAAATAGGCAGGGGGCATTAACTG
TTTATACGGGCACTGTTACTCAAGGCACTGACCCCGTTAAAACTTATTACCAGTACACTCCTGTATCATCAAAAGCC
ATGTATGACGCTTACTGGAACGGTAAATTCAGAGACTGCGCTTTCCATTCTGGCTTTAATGAGGATTTATTTGTTTG
TGAATATCAAGGCCAATCGTCTGACCTGCCTCAACCTCCTGTCAATGCTGGCGGCGGCTCTGGTGGTGGTTCTGGTG
GCGGCTCTGAGGGTGGTGGCTCTGAGGGTGGCGGTTCTGAGGGTGGCGGCTCTGAGGGAGGCGGTTCCGGTGGTGGC
TCTGGTTCCGGTGATTTTGATTATGAAAGATGGCAAACGCTAATAAGGGGGCTATGACCGAAAATGCCGATGAAAA
CGCGCTACAGTCTGACGCTAAAGGCAAACTTGATTCTGTCGCTACTGATTACGGTGCTGCTATCGATGGTTTCATTG
GTGACGTTTCCGGCCTTGCTAATGGTAATGGTGCTACTGGTGATTTTGCTGGCTCTAATTCCCAAATGGCTCAAGTC
GGTGACGGTGATAATTCACCTTTAATGAATAATTTCCGTCAATATTTACCTTCCCTCCCTCAATCGGTTGAATGTCG
CCCTTTTGTCTTTGGCGCTGGTAAACCATATGAATTTTCTATTGATTGTGACAAAATAAACTTATTCCGTGGTGTCT
TTGCGTTTCTTTTATATGTTGCCACCTTTATGTATGTATTTTCTACGTTTGCTAACATACTGCGTAATAAGGAGTCT
TAATCATGCCAGTTCTTTTGGGTATTCCGTTATTATTGCGTTTCCTCGGTTTCCTTCTGGTAACTTTGTTCGGCTAT
CTGCTTACTTTTCTTAAAAAGGGCTTCGGTAAGATAGCTATTGCTATTTCATTGTTTCTTGCTCTTATTATTGGGCT
TAACTCAATTCTTGTGGGTTATCTCTCTGATATTAGCGCTCAATTACCCTCTGACTTTGTTCAGGGTGTTCAGTTAA
TTCTCCCGTCTAATGCGCTTCCCTGTTTTATGTTATTCTCTCTGTAAAGGCTGCTATTTTCATTTTTGACGTTAAA
CAAAAAATCGTTTCTTATTTGGATTGGGATAAATAATATGGCTGTTTATTTTGTAACTGGCAAATTAGGCTCTGGAA
AGACGCTCGTTAGCGTTGGTAAGATTCAGGATAAAATTGTAGCTGGGTGCAAAATAGCAACTAATCTTGATTTAAGG
CTTCAAAACCTCCCGCAAGTCGGGAGGTTCGCTAAAACGCCTCGCGTTCTTAGAATACCGGATAAGCCTTCTATATC
TGATTTGCTTGCTATTGGGCGCGGTAATGATTCCTACGATGAAAATAAAAACGGCTTGCTTGTTCTCGATGAGTGCG
GTACTTGGTTTAATACCCGTTCTTGGAATGATAAGGAAAGACAGCCGATTATTGATTGGTTTCTACATGCTCGTAAA
TTAGGATGGGATATTATTTTTCTTGTTCAGGACTTATCTATTGTTGATAAACAGGCGCGTTCTGCATTAGCTGAACA
TGTTGTTTATTGTCGTCGTCTGGACAGAATTACTTTACCTTTTGTCGGTACTTTATATTCTCTTATTACTGGCTCGA
AAATGCCTCTGCCTAAATTACATGTTGGCGTTGTTAAATATGGCGATTCTCAATTAAGCCCTACTGTTGAGCGTTGG
CTTTATACTGGTAAGAATTTGTATAACGCATATGATACTAAACAGGCTTTTTCTAGTAATTATGATTCCGGTGTTTA
TTCTTATTTAACGCCTTATTTATCACACGGTCGGTATTTCAAACCATTAAATTTAGGTCAGAAGATGAAATTAACTA
AAATATATTTGAAAAAGTTTTCTCGCGTTCTTTGTCTTGCGATTGGATTTGCATCAGCATTTACATATAGTTATATA
ACCCAACCTAAGCCGGAGGTTAAAAAGGTAGTCTCTCAGACCTATGATTTTGATAAATTCACTATTGACTCTTCTCA
GCGTCTTAATCTAAGCTATCGCTATGTTTTCAAGGATTCTAAGGGAAAATTAATTAATAGCGACGATTTACAGAAGC
```

FIG. 2, continued

```
AAGGTTATTCACTCACATATATTGATTTATGTACTGTTTCCATTAAAAAAGGTAATTCAAATGAAATTGTTAAATGT
AATTAATTTTGTTTTCTTGATGTTTGTTTCATCATCTTCTTTTGCTCAGGTAATTGAAATGAATAATTCGCCTCTGC
GCGATTTTGTAACTTGGTATTCAAAGCAATCAGGCGAATCCGTTATTGTTTCTCCCGATGTAAAAGGTACTGTTACT
GTATATTCATCTGACGTTAAACCTGAAAATCTACGCAATTTCTTTATTTCTGTTTTACGTGCAAATAATTTTGATAT
GGTAGGTTCTAACCCTTCCATTATTCAGAAGTATAATCCAAACAATCAGGATTATATTGATGAATTGCCATCATCTG
ATAATCAGGAATATGATGATAATTCCGCTCCTTCTGGTGGTTTCTTTGTTCCGCAAAATGATAATGTTACTCAAACT
TTTAAAATTAATAACGTTCGGGCAAAGGATTTAATACGAGTTGTCGAATTGTTTGTAAAGTCTAATACTTCTAAATC
CTCAAATGTATTATCTATTGACGGCTCTAATCTATTAGTTGTTAGTGCTCCTAAAGATATTTTAGATAACCTTCCTC
AATTCCTTTCAACTGTTGATTTGCCAACTGACCAGATATTGATTGAGGGTTTGATATTTGAGGTTCAGCAAGGTGAT
GCTTTAGATTTTTCATTTGCTGCTGGCTCTCAGCGTGGCACTGTTGCAGGCGGTGTTAATACTGACCGCCTCACCTC
TGTTTTATCTTCTGCTGGTGGTTCGTTCGGTATTTTTAATGGCGATGTTTTAGGGCTATCAGTTCGCGCATTAAAGA
CTAATAGCCATTCAAAAATATTGTCTGTGCCACGTATTCTTACGCTTTCAGGTCAGAAGGGTTCTATCTCTGTTGGC
CAGAATGTCCCTTTTATTACTGGTCGTGTGACTGGTGAATCTGCCAATGTAAATAATCCATTTCAGACGATTGAGCG
TCAAAATGTAGGTATTTCCATGAGCGTTTTTCCTGTTGCAATGGCTGGCGGTAATATTGTTCTGGATATTACCAGCA
AGGCCGATAGTTTGAGTTCTTCTACTCAGGCAAGTGATGTTATTACTAATCAAAGAAGTATTGCTACAACGGTTAAT
TTGCGTGATGGACAGACTCTTTTACTCGGTGGCCTCACTGATTATAAAAACACTTCTCAGGATTCTGGCGTACCGTT
CCTGTCTAAAATCCCTTTAATCGGCCTCCTGTTTAGCTCCCGCTCTGATTCTAACGAGGAAAGCACGTTATACGTGC
TCGTCAAAGCAACCATAGTACGCGCCCTGTAGCGGCGCATTAAGCGCGGCGGGTGTGGTGGTTACGCGCAGCGTGAC
CGCTACACTTGCCAGCGCCCTAGCGCCCGCTCCTTTCGCTTTCTTCCCTTCCTTTCTCGCCACGTTCGCCGGCTTTC
CCCGTCAAGCTCTAAATCGGGGGCTCCCTTTAGGGTTCCGATTTAGTGCTTTACGGCACCTCGACCCCAAAAAACTT
GATTTGGGTGATGGTTCACGTAGTGGGCCATCGCCCTGATAGACGGTTTTTCGCCCTTTGACGTTGGAGTCCACGTT
CTTTAATAGTGGACTCTTGTTCCAAACTGGAACAACACTCAACCCTATCTCGGGCTATTCTTTTGATTTATAAGGGA
TTTTGCCGATTTCGGAACCACCATCAAACAGGATTTTCGCCTGCTGGGGCAAACCAGCGTGGACCGCTTGCTGCAAC
TCTCTCAGGGCCAGGCGGTGAAGGGCAATCAGCTGTTGCCCGTCTCACTGGTGAAAAGAAAAACCACCCTGGCGCCC
AATACGCAAACCGCCTCTCCCCGCGCGTTGGCCGATTCATTAATGCAGCTGGCACGACAGGTTTCCCGACTGGAAAG
CGGGCAGTGAGCGCAACGCAATTAATGTGAGTTAGCTCACTCATTAGGCACCCCAGGCTTTACACTTTATGCTTCCG
GCTCGTATGTTGTGTGGAATTGTGAGCGGATAACAATTTCACACAGGAAACAGCTATGACCATGATTACGAATTCGA
GCTCGGTACCCGGGGATCCTTATACGGGTACTAGCCATGCGTATACGGTCGCTAGCGGACTTGCCTCGCTATCAAAG
GTCTAGAGTCGACCTGCAGGCATGCAAGCTTGGCACTGGCCGTCGTTTTACAACGTCGTGACTGGGAAAACCCTGGC
GTTACCCAACTTAATCGCCTTGCAGCACATCCCCCTTTCGCCAGCTGGCGTAATAGCGAAGAGGCCCGCACCGATCG
CCCTTCCCAACAGTTGCGCAGCCTGAATGGCGAATGGCGCTTTGCCTGGTTTCCGGCACCAGAAGCGGTGCCGGAAA
GCTGGCTGGAGTGCGATCTTCCTGAGGCCGATACTGTCGTCGTCCCCTCAAACTGGCAGATGCACGGTTACGATGCG
CCCATCTACACCAACGTGACCTATCCCATTACGGTCAATCCGCCGTTTGTTCCCACGGAGAATCCGACGGGTTGTTA
CTCGCTCACATTTAATGTTGATGAAAGCTGGCTACAGGAAGGCCAGACGCGAATTATTTTTGATGGCGTTCCTATTG
GTTAAAAAATGAGCTGATTTAACAAAAATTTAATGCGAATTTTAACAAAAATATTAACGTTTACAATTTAAATATTTG
CTTATACAATCTTCCTGTTTTGGGGCTTTTCTGATTATCAACCGGGGTACATATGATTGACATGCTAGTTTTACGA
TTACCGTTCATCGATTCTCTTGTTTGCTCCAGACTCTCAGGCAATGACCTGATAGCCTTTGTAGATCTCTCAAAAAT
AGCTACCCTCTCCGGCATTAATTTATCAGCTAGAACGGTTGAATATCATATTGATGGTGATTTGACTGTCTCCGGCC
TTTCTCACCCTTTTGAATCTTTACCTACACATTACTCAGGCATTGCATTTAAAATATATGAGGGTTCTAAAAATTTT
TATCCTTGCGTTGAAATAAAGGCTTCTCCCGCAAAAGTATTACAGGGTCATAATGTTTTTGGTACAACCGATTTAGC
TTTATGCTCTGAGGCTTTATTGCTTAATTTTGCTAATTCTTTGCCTTGCCTGTATGATTTATTGGATGTT
```

FIG. 3

| Strand | SEQ ID NO: | Description | Sequence |
|---|---|---|---|
| 1 | 2 | core | TTTAGTTAATTTCAATTAATTTTCCCTTTGAGTGA |
| 2 | 3 | core | AGAAAACTTTTTCATTGAAAACATAGCG |
| 3 | 4 | core | AATCGCAAGACAAAAGATTAAGACGCTG |
| 4 | 5 | core | GTTATATTCATAGGTCTGAGACATCAAGAAAACAAATTTCAA |
| 5 | 6 | core | TGAATTTTACATTTAACAATTTCGCGCA |
| 6 | 7 | core | ATAACCTCCTTTTACATCGGGTTTCAGGTTTAACGAAAAGTT |
| 7 | 8 | core | ACAATATATGAGAATCCAATATAT |
| 8 | 9 | core | ATTCGCCAAATAAAGAAATTGATTTTGC |
| 9 | 10 | core | TGCATGGAAAATAGCTTGAACGCG |
| 10 | 11 | core | AAATCATTTGAGAAGAGCAAATCC |
| 11 | 12 | core | GAGGCGAGGTTAGAACCTACCATCATAT |
| 12 | 13 | core | TTACCTGTATACTTCTGAATATGATGGC |
| 13 | 14 | core | TGAGTAAACTCGTATTAAATCCAGAGATACATCGCCATTA |
| 14 | 15 | core | GGAACAAGACTTTACAAACAACTGAAAGGCGCGAAAGATAAA |
| 15 | 16 | core | GGAGCGGTTTGAGGATTTAGAGCACAGACAATAATCTCAATC |
| 16 | 17 | core | TCCTGATGAGCCGTCAATAGACAGTTGGATCAAACAACAGTG |
| 17 | 18 | core | AATTCATGCACTAACAACTAAAAAGGAATCACCTTAGCAGCA |
| 18 | 19 | core | TAAAGCATTGAGGATGCAACAGGAAAAATTGC |
| 19 | 20 | core | AAAATACCGAACGAACCACCAGTGAGAATTAACCGTTGTAATTC |
| 20 | 21 | core | AGACTGATAGCCCTAAAAGAACCCAGTCACA |
| 21 | 22 | core | ACAGAGGCCTGAGATTCTTTGATTAGTAATGG |
| 22 | 23 | core | GCGTATTAGTCTTTAATCGTAAGAATTTACA |
| 23 | 24 | core | TTAACACACAGGAACACTTGCCTGAGTATTTG |
| 24 | 25 | core | CCACGCTGGCCGATTCAAACTATCGGCCCGCT |
| 25 | 26 | core | GCCGCTGAACCTCAAATCAAATCAGGAAATA |
| 26 | 27 | core | AATGAAACAGAGCGTAATATC |
| 27 | 28 | core | CGACCAGTCACGCAGCCACCGCTGGCAAAGCGAAAGAAC |
| 28 | 29 | core | ACCTTCTGACTTCGACACATTATCCGTAGATAGAA |
| 29 | 30 | core | TTGGCAGGCAATACAGTGTTTCTGCGCGGGCG |
| 30 | 31 | core | ATTATACGTGAGTATTAAGAAACCAAAACAGTGAT |
| 31 | 32 | core | GTCTGAAATAACATCGGTACGGCCGCGCACGG |
| 32 | 33 | core | ACGATCTGGTTAATACAAATTATCATATCAATACA |
| 33 | 34 | core | CCTACATGAAGAACTAAAGGGCAGGGCGGAGCCCCGGGC |
| 34 | 35 | core | CATACAGTTGTAGATTATATCAGAATGGAAGATTA |
| 35 | 36 | core | TGGGGAGCTATTTGACGACTAAATACCATCAGTTT |
| 36 | 37 | core | GGAAGAAGTGTAGCGGTCACGTTATAATCAGC |
| 37 | 38 | core | AGAGAACGTGAATCAAATGCGTATTTCCAGTCCCC |
| 38 | 39 | core | CGAACGTTAACCACCACACCCCCAGAATTGAG |
| 39 | 40 | core | GGAAGGGCGAAAATCGGGTTTTTCGCGTTGCTCGT |
| 40 | 41 | core | GAGCTTGTTAATGCGCCGCTAATTTTAGCGCCTGCCCTCAAT |
| 41 | 42 | core | CTAAAGGCGTACTATGGTTGCAACAGGAGAGA |
| 42 | 43 | core | GCCGTAAAGCAGCACGTATAA |

FIG. 3 (cont.)

| Strand | SEQ ID NO: | Description | Sequence |
|---|---|---|---|
| 43 | 44 | core | AAGTAGGGTTAACGCGCTGCCAGCGGCTAGTAGTCCGC |
| 44 | 45 | core | GATTCCTGTTACGGGCAGTGAGCTTTTCCTGAACGACG |
| 45 | 46 | core | GCCTTCACCGAAAGCCTCCGCTCATTCCCAG |
| 46 | 47 | core | GTCCACGCTGCCCAAATCAAG |
| 47 | 48 | core | GGCGGTTAGAATAGCCCGAGAAGTCCACTATTAAAAAGGAAG |
| 48 | 49 | core | CAGGGTGCAAAATCCCTTATAGACTCCAACGTCAAAAGCCGG |
| 49 | 50 | core | CAGTGAGTGATGGTGGTTCCGAAAACCGTCTATCACGATTTA |
| 50 | 51 | core | ATTGCCCCCAGCAGGCGAAAAGGCCCACTACGTGACGGAACC |
| 51 | 52 | core | AAATGCCAGTTTGAGGGGGATTGAGTGAGCGAATAGGA |
| 52 | 53 | core | GGGTAGACCTTTGATAGATTAAATCCGTAAT |
| 53 | 54 | core | CTCGAATGCTCACTACAGTAT |
| 54 | 55 | core | AATTGCATGCCTGCAGGACCCGTCGGATTTCAAATCAG |
| 55 | 56 | core | GCTCATGGTCATAGCTGAACTCACTCGCACT |
| 56 | 57 | core | TAATGTGAAATTGTTATGGGGTGCGGCACCG |
| 57 | 58 | core | TCACGACTGTGCTGGCGCAAC |
| 58 | 59 | core | AACGCCAGGGTTCAATTCCACACAACATACG |
| 59 | 60 | core | GGGATAGGTGCATCCCTGTCGGGGGAGA |
| 60 | 61 | core | AAACGGCGACGACGGCCCGCTTGGGCGC |
| 61 | 62 | core | CGGGCCTAGGAAGAATTAATTTTTTCAC |
| 62 | 63 | core | TGTTGGGGCTTTCCCTAATGAACAGCTG |
| 63 | 64 | core | TCGCCATTGCCGGAAAAGTGTCCTGGCC |
| 64 | 65 | core | CGTAACCGTCACGTCAGCTTTAATTCGC |
| 65 | 66 | core | CCAGCCAAAGGGCGTGGCGAAAATTCGC |
| 66 | 67 | core | CTTCTGGTCAGGCTCAAGGCGTAAACGT |
| 67 | 68 | core | AATCATCAACCGAGGCAACCCGTATAAGGATCGGG |
| 68 | 69 | core | ACGCCATGAACGGTAATCGTAGAGATCTACAAAGGTAAAAAT |
| 69 | 70 | core | CTCATTTCATGTCAATCATATGGAGAGGGTAGCTATATATTT |
| 70 | 71 | core | ATTAAATGGTTGATAATCAGATCTAGCTGATAAATGAGTAAT |
| 71 | 72 | core | TAATATTCAAAAACAGGAAGAATCAATATGATATTTCAAAAG |
| 72 | 73 | core | ATATTTAAATTGATTAAGTTGGGT |
| 73 | 74 | core | ACAAGAGGTCATTGCCTGAGAGCCTTTATTTCAACAATACTT |
| 74 | 75 | core | TGAAAACTAGTTTAACCAGTAACATCGACTCTACCGAG |
| 75 | 76 | core | GCCGTACCCCTTTTGTTGCTATTACCAA |
| 76 | 77 | core | TTTTAGACCAAAAACATTATGCAATAAC |
| 77 | 78 | core | TAAATGCCATAAAGCTAAATCTTTCATTTGGGGCG |
| 78 | 79 | core | GGTGAGACAAGGCAAAGAATT |
| 79 | 80 | core | AGCAAAATAAAGATCAACCGTAAAGCCCTTGTTAAGGGGGAGTTG |
| 80 | 81 | core | ATTTCGCAAATGGTACCCTGTGCAAGGACTATCAGAATCGATCAAA |
| 81 | 82 | core | CTGTTTAGCTATATGGTTGTAACCCTCATTTT |
| 82 | 83 | core | CGAGCTGCTCAGAGAATGCCTTAAT |
| 83 | 84 | core | TAGATTAGTTTGAAACCAGAGCGTTTTAGGG |
| 84 | 85 | core | CCATATATACCTTTCATCAAACTGCGGACCCT |
| 85 | 86 | core | TTTTAAATGGCTTAGGTCTTTCTTTAAACAAA |

FIG. 3 (cont.)

| Strand | SEQ ID NO: | Description | Sequence |
|---|---|---|---|
| 86 | 87 | core | AGGGCCCGAATAGACTGTAAAAACAAATCTATCAT |
| 87 | 88 | core | TAGAGAGACAGTTGATTCCCAATTCTGCCAAC |
| 88 | 89 | core | CCTTTTGCTGGAAGTTTCATT |
| 89 | 90 | core | TCAAAAATCAGAGCTTAATTG |
| 90 | 91 | core | GGTGCTTTTGCAGTCAGGATTTTAACAG |
| 91 | 92 | core | AAATGTTAGACTTCAAATATCCCGGAAGCAAACTCGAACGAG |
| 92 | 93 | core | TGAGTAAGAGCAGGTAGGAGTAGTCAAGAACAATC |
| 93 | 94 | core | ACGACGAGATAGCGTCCAATAAAGATTAAGAGGAATCAGGAT |
| 94 | 95 | core | CGTACTAACGATGGTTTCTTCATCTACTTAGGAGG |
| 95 | 96 | core | ATCATAAATCGTCATAAATATAGCAAAGCGGATTGAATTGCT |
| 96 | 97 | core | AGGCATAATCCCCCTCAAATGACCCTGACTATTATGTCATTT |
| 97 | 98 | core | AGGTGAGATTCCTGACGCCAAATCTCGCCTGCGAT |
| 98 | 99 | core | TACATAACGCCAGTTCAGAAA |
| 99 | 100 | core | CTTATGCGACGTTGGGAAGAACAAAATAGCGAGAGAATAGTA |
| 100 | 101 | core | TGTCAGGCGCAGACGGTAGGCACCTGAGGAC |
| 101 | 102 | core | ACTTTAACGTTAATAAAACGATTACCAG |
| 102 | 103 | core | GCTTGAGGAACAACATTATTACAACACT |
| 103 | 104 | core | CCAGAACAAAGATTCATCAGTAATTACG |
| 104 | 105 | core | GGCTTGCTAGGAATACCA |
| 105 | 106 | core | ATGCCGAACTAAATACGTGAGGAA |
| 106 | 107 | core | CGCACACTCAAAGACAGCATCGGAATATGACAACAACC |
| 107 | 108 | core | AACGAAACCGGAACTTTTTCACGTTGAAGGGA |
| 108 | 109 | core | CAATAGCAACGGCTACATTTCCAGTGCTAAA |
| 109 | 110 | core | CACTAAAGACCTGCAAAAAAAGGCTCCGTTGCGCC |
| 110 | 111 | core | CCCCCAGATAAATTGCCTTTAATTGTATTTAA |
| 111 | 112 | core | TATGATCGTCACCCTCAACGCATAGCTTGATACCGATAAAAA |
| 112 | 113 | core | TCATAATGCCACTACGACAATCATAAAGGAATTGCGAACAAC |
| 113 | 114 | core | TAAAGACACGATCTTTCAGCGGAGTGAG |
| 114 | 115 | core | GGCCGCTTCGCTGATCGAGGTGAATTTCCGGTTTATGTATCAAACGTAA |
| 115 | 116 | core | AGTAAAGTTTTCACCAGTACAAACGGATAAG |
| 116 | 117 | core | CAACTTTTAATAATGAGGCGC |
| 117 | 118 | core | GACATTTCTGTATAATCTCCTCCATGT |
| 118 | 119 | core | ACAACCGATACCACCCTCATTTTCGGAGGTT |
| 119 | 120 | core | AAAGGAACAACTAAGGGAAAACGGTGTACAGACGAATTAC |
| 120 | 121 | core | GGAGTGTCGACGGATATTCATTACAGAAACA |
| 121 | 122 | core | CATTAAATGAACGAGGGAAGAATA |
| 122 | 123 | core | GAACCGCCACCCTCTCAGAAC |
| 123 | 124 | core | TGCCGTCAGAGGCTGAGACTCCCAGAATGGAAAGCGGTTGAG |
| 124 | 125 | core | GGGAGTTTCGTGTCGTCGAGGCTTAACCTAA |
| 125 | 126 | core | AAGTATATTCTGAAACATGAACTGAATTTACCGTTCCGCCGCCAG |
| 126 | 127 | core | TATCACCTGCCTATTTCGGAAGCGTCATACATGGCCCACCAG |
| 127 | 128 | core | TCAAGGGATAATCGCCCGCAGCGATCTTTGA |
| 128 | 129 | core | TAGTACCGTATAAACAGTTAAGATACAGGAGTGTAGAGCCAC |

FIG. 3 (cont.)

| Strand | SEQ ID NO: | Description | Sequence |
|---|---|---|---|
| 129 | 130 | core | CCCAGAGCCATATTCGGTTTGCGGACCAAGC |
| 130 | 131 | core | AAGCTCAAGAACCAGGCTACAACGTAGCGTATTTT |
| 131 | 132 | core | GCAGGTCAACCGATTTGGGAAACCATTA |
| 132 | 133 | core | AACCACCCAATAATCAAAATCTATAAAA |
| 133 | 134 | core | CACCCTCCCAGAGCCCCTTATGACAGAA |
| 134 | 135 | core | AACCGCCCCTCCCTTCGGCATAGCGTCA |
| 135 | 136 | core | ATTACCAGAGCCAGTAACCTATTAGCCCGGAAACC |
| 136 | 137 | core | GCAAGGCGAAACAATAGCCGAACAAAGTTATT |
| 137 | 138 | core | AACCCGACTTGAGCCATTGAGGGATCACAAT |
| 138 | 139 | core | ATGAAACTAAGCCCAGGAAACCGAGGAAAAAGACAAATT |
| 139 | 140 | core | GATAAAGGTGAATTATCTGACGGACCACGGA |
| 140 | 141 | core | CCGTAATGATAACCAATAACGGAATACCGGCA |
| 141 | 142 | core | TCAAGTTATTGAGCACTGGCATGATTAAAGAA |
| 142 | 143 | core | TTTTTTCGGTCATAGCCCACCACCACATACATAAAGGTCAAAAGAGCTA |
| 143 | 144 | core | CAATAGAAAGCAGATGAAATAAAACGATAGTT |
| 144 | 145 | core | TTGGGGAAGGGACAGGAGCAGTCTAGTATTAGAGA |
| 145 | 146 | core | ATAAGTTTACCAGAAATAATACAAAAATCTTT |
| 146 | 147 | core | GAAACGCACGCAATCACAAGATTACAGACTTACCATTCTAAGCATT |
| 147 | 148 | core | ACAACCGGAAAGAGCCGTTTTGATTGCCCCCGTAC |
| 148 | 149 | core | AATGGAACCGACCCTCACTGGTAAAGTGCCCGCCA |
| 149 | 150 | core | CAAACGTGACTCCTAAAGTCAGGAGAATATTA |
| 150 | 151 | core | GAAAAGTAAATTCAGACATTCAGACGATATTA |
| 151 | 152 | core | ATAAACAGGGAGCTACATAGCGAATAATCGGATAGATA |
| 152 | 153 | core | AAATAAGGCAATAGCACCATTTTAGAGCCAGCAAAAAGGGCTATGGTT |
| 153 | 154 | core | ACAGCCCAATGAACAAGCTGTCCACCAGTAACCGACCG |
| 154 | 155 | core | ATTTGCCTTTTTGTTTAACGTAGAGCAACGGA |
| 155 | 156 | core | CCAATATAGAACCAAGTACAACATTTAGGCACGTTAAA |
| 156 | 157 | core | CGAGCGTGAAAATAGCAGCCTATTGAGTCATC |
| 157 | 158 | core | CCTGAATGAGAATAACATAAATCAGAGACAGTAGCTAGCGTT |
| 158 | 159 | core | TGCACCCAAGCGCATTAGACGGAGGGTATGCC |
| 159 | 160 | core | GTTGGAGGTTGAGCATGAAAATAA |
| 160 | 161 | core | ATCATTACCGCAAATAAACAGC |
| 161 | 162 | core | TCATCGAAGCAAGCAAATCAGGAGCCTA |
| 162 | 163 | core | GTATTAAAGGCTTATCCGGTAACGCTAA |
| 163 | 164 | core | CCAGAACGCGTTAACAAGGAATCA |
| 164 | 165 | core | TCCTTATAACGCGAGGCGTTTATTTTAT |
| 165 | 166 | core | CAATCAACCTCCCGACTTGCGGCTATTT |
| 166 | 167 | core | AAGGTAAAGTAATTCAAGCCG |
| 167 | 168 | core | TTTCGAGGACGACGACAATAAACCGCAC |
| 168 | 169 | core | ATGTAATGTTCAGCTAATGCAAGAACGG |
| 169 | 170 | core | GCCATATCCTGTTTATCAACACTGTCTT |
| 170 | 171 | core | AGTAGGGAGTCCTGAACAAGATAGAAAC |
| 171 | 172 | core | GGTTTGAAATATAAGAGAATAT |

FIG. 3 (cont.)

| Strand | SEQ ID NO: | Description | Sequence |
|---|---|---|---|
| 172 | 173 | core | TGTGATAAATAAGGGAGGCAT |
| 173 | 174 | core | TAAGAATAAACACCCGCCAAC |
| 174 | 175 | core | TAATTACTAGAAAAGAGAATC |
| 175 | 176 | FRET-site-A1 | TTCAATTAATATCAAAAAACTATA |
| 176 | 177 | FRET-site-A2 | TTAGTATCATATGCGCTCAAC |
| 177 | 178 | FRET-site-B1 | CTAAAGTACGGTGTATAAGAGAGTCAGATCAT |
| 178 | 179 | FRET-site-B2 | GTGTAGGTTAAGCAATAAAGCAAAAGGTGGCATCA |
| 179 | 180 | internal handle | CAGTACATAAATCAATAACGGTTGTGCTACTCCAGTTC |
| 180 | 181 | internal handle | AATTACCTTTTTTATTTGAATTTGTGCTACTCCAGTTC |
| 181 | 182 | internal handle | CATTTTTGAATGGCGTCAGTATTGTGCTACTCCAGTTC |
| 182 | 183 | internal handle | GCCAGTGCGCCAGCATCGGTGTTGTGCTACTCCAGTTC |
| 183 | 184 | internal handle | CGGCCTCCTCTCCGTGGGAACTTGTGCTACTCCAGTTC |
| 184 | 185 | internal handle | ATAGGCTGGCTGACAATTTCATTGTGCTACTCCAGTTC |
| 185 | 186 | internal handle | AAGAGTAATCTTGAAAATTGGTTGTGCTACTCCAGTTC |
| 186 | 187 | internal handle | GCAAGCCCAATAGGATAGGTGTTGTGCTACTCCAGTTC |
| 187 | 188 | internal handle | CATTTAAATATACCGTCAGTCACCATTGTGCTACTCCAGTTC |
| 188 | 189 | internal handle | TGCCATCTTTTCTTAGCAGCATTGTGCTACTCCAGTTC |
| 189 | 190 | internal handle | ACCAAGTAATTATTTGCACGTACCAGAATTGTGCTACTCCAGTTC |
| 190 | 191 | internal handle | TTTACGTTAGGTACCGTAACACTGTTGATATTTGTGCTACTCCAGTTC |
| 191 | 192 | support staple 1 | CTTAATTAGCCTGTTGTAAATGCTGATGTCAATAGCATCATGG |
| 192 | 193 | support staple 2 | TTGCGGATATGCAAATTCTACTAATAGTGCTGACGT |
| 193 | 194 | PDGF aptamer 1 | CCAACGTTATACAAATTCTTATACTCAGGGCACTGCAAGCAATTGTGGTCCCAATGGGCTGAGTA |
| 194 | 195 | PDGF aptamer 2 | AGTAGCATTAACATCCAATTACTCAGGGCACTGCAAGCAATTGTGGTCCCAATGGGCTGAGTA |
| 195 | 196 | PDGF aptamer complement 1 | TACTCAGCCCATTGGGACCACAATTGCTTGCAGTGCCCTGAGTAAACCTCCGGCTTAGGTTGG |
| 196 | 197 | PDGF aptamer complement 2 | TACTCAGCCCATTGGGACCACAATTGCTTGCAGTGCCCTGAGTAAATGCTGTAGCTCAACATG |
| 197 | 198 | random aptamer latch 1 | AGTAGCATTAACATCCAATTAACAGGGTCGCCCATCGGTTCGAATCAGACGGTTTAAGGCAGT |
| 198 | 199 | random aptamer latch 2 | CCAACGTTATACAAATTCTTATAACAGGGTCGCCCATCGGTTCGAATCAGACGGTTTAAGGCAGT |
| 199 | 200 | random aptamer complement 1 | ACTGCCTTAAACCGTCTGATTCGAACCGATGGGCGACCCTGTTAAATGCTGTAGCTCAACATG |
| 200 | 201 | random aptamer complement 2 | ACTGCCTTAAACCGTCTGATTCGAACCGATGGGCGACCCTGTTAAACCTCCGGCTTAGGTTGG |
| 201 | 202 | aptamer TC01 | CCAACGTTATACAAATTCTTAACCAAACACAGATGCAACCTGACTTCTAACGTCATTTGGTG |
| 202 | 203 | aptamer tc01 1 complement | CACCAAATGACGTTAGAAGTCAGGTTGCATCTGTGTTTGGTAACCTCCGGCTTAGGTTGG |
| 203 | 204 | aptamer TC01 2 | AGTAGCATTAACATCCAATACCAAACACAGATGCAACCTGACTTCTAACGTCATTTGGTG |

FIG. 3 (cont.)

| Strand | SEQ ID NO: | Description | Sequence |
|---|---|---|---|
| 204 | 205 | aptamer tc01 2 complement | CACCAAATGACGTTAGAAGTCAGGTTGCATCTGTGTTTGGTAATGCTGTA GCTCAACATG |
| 205 | 206 | aptamer TD05 1 | CCAACGTTATACAAATTCTTAAACACCGTGGAGGATAGTTCGGTGGCTGT TCAGGGTCTCCTCCCGGTG |
| 206 | 207 | aptamer td05 1 complement | CACCGGGAGGAGACCCTGAACAGCCACCGAACTATCCTCCACGGTGTTAA CCTCCGGCTTAGGTTGG |
| 207 | 208 | aptamer TD05 2 | AGTAGCATTAACATCCAATAACACCGTGGAGGATAGTTCGGTGGCTGTTC AGGGTCTCCTCCCGGTG |
| 208 | 209 | aptamer td05 2 complement | CACCGGGAGGAGACCCTGAACAGCCACCGAACTATCCTCCACGGTGTTAA TGCTGTAGCTCAACATG |
| 209 | 210 | aptamer TE13 1 | CCAACGTTATACAAATTCTTAAGGCCCCCAGGCTCGGTGGATGCAAACAC ATGACTATGGGCCCGT |
| 210 | 211 | aptamer te13 1 complement | ACGGGCCCATAGTCATGTGTTTGCATCCACCGAGCCTGGGGGCCTAACCT CCGGCTTAGGTTGG |
| 211 | 212 | aptamer TE13 2 | AGTAGCATTAACATCCAATAGGCCCCCAGGCTCGGTGGATGCAAACACAT GACTATGGGCCCGT |
| 212 | 213 | aptamer te13 2 complement | ACGGGCCCATAGTCATGTGTTTGCATCCACCGAGCCTGGGGGCCTAATGC TGTAGCTCAACATG |
| 213 | 214 | aptamer TE17 1 | CCAACGTTATACAAATTCTTACAGCTACGCAATACAAAACTCCGAACACC TGCTTCTGACTGGGTGCTG |
| 214 | 215 | aptamer te17 1 complement | CAGCACCCAGTCAGAAGCAGGTGTTCGGAGTTTTGTATTGCGTAGCTGAA CCTCCGGCTTAGGTTGG |
| 215 | 216 | aptamer TE17 2 | AGTAGCATTAACATCCAATCAGCTACGCAATACAAAACTCCGAACACCTG CTTCTGACTGGGTGCTG |
| 216 | 217 | aptamer te17 2 complement | CAGCACCCAGTCAGAAGCAGGTGTTCGGAGTTTTGTATTGCGTAGCTGAA TGCTGTAGCTCAACATG |
| 217 | 218 | support staple removal str. 1 | CCATGATGCTATTGACATCAGCATTTACAACAGGCTAATTAAG |
| 218 | 219 | support staple removal str. 2 | ACGTCAGCACTATTAGTAGAATTTGCATATCCGCAA |
| 219 | 220 | handle-linker with 5´ BioTEG | /5BioTEG/GAACTGGAGTAGCAC |
| 220 | 221 | handle-linker with 5´ Amine | /5AmMC6/GAACTGGAGTAGCAC |
| 221 | 222 | handle-linker with 5´ Thiol | /5ThioMC6-D/GAACTGGAGTAGCAC |
| 222 | 223 | handle-linker with 5´ Dithiol | /5DTPA/GAACTGGAGTAGCAC |
| 223 | 224 | FRET-site-A1+FAM | TTCAATTAATATCAAAAAACTATAT/36-FAM/ |
| 224 | 225 | FRET-site-A2+Quencher | /5IAbFQ/TTTAGTATCATATGCGCTCAAC |
| 225 | 226 | FRET-site-B1+TYE665 | /5TYE665/TCTAAAGTACGGTGTATAAGAGAGTCAGATCAT |
| 226 | 227 | FRET-site-B2+Quencher | GTGTAGGTTAAGCAATAAAGCAAAAGGTGGCATCAT/3IAbRQSp/ |

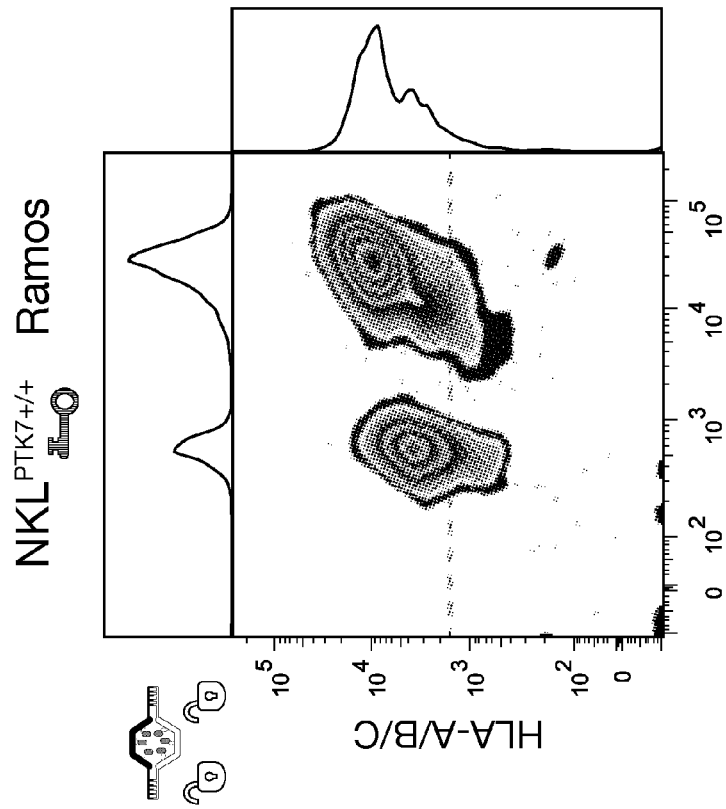
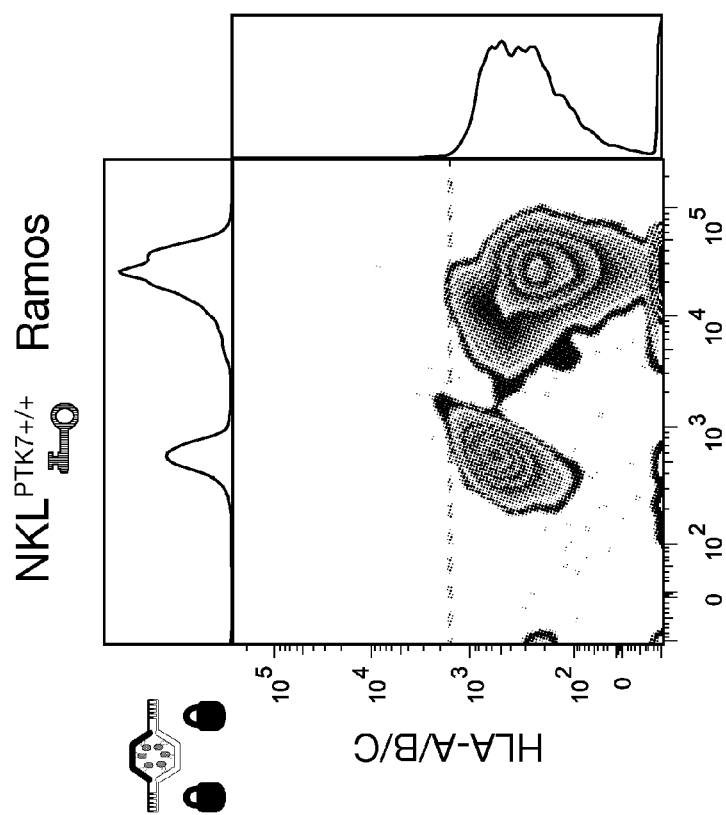
FIG. 4E
FIG. 4D

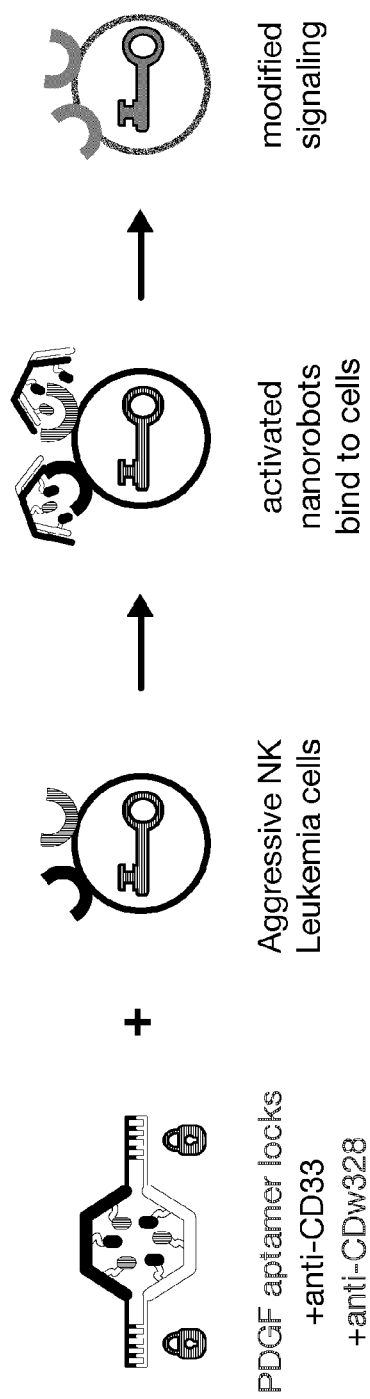
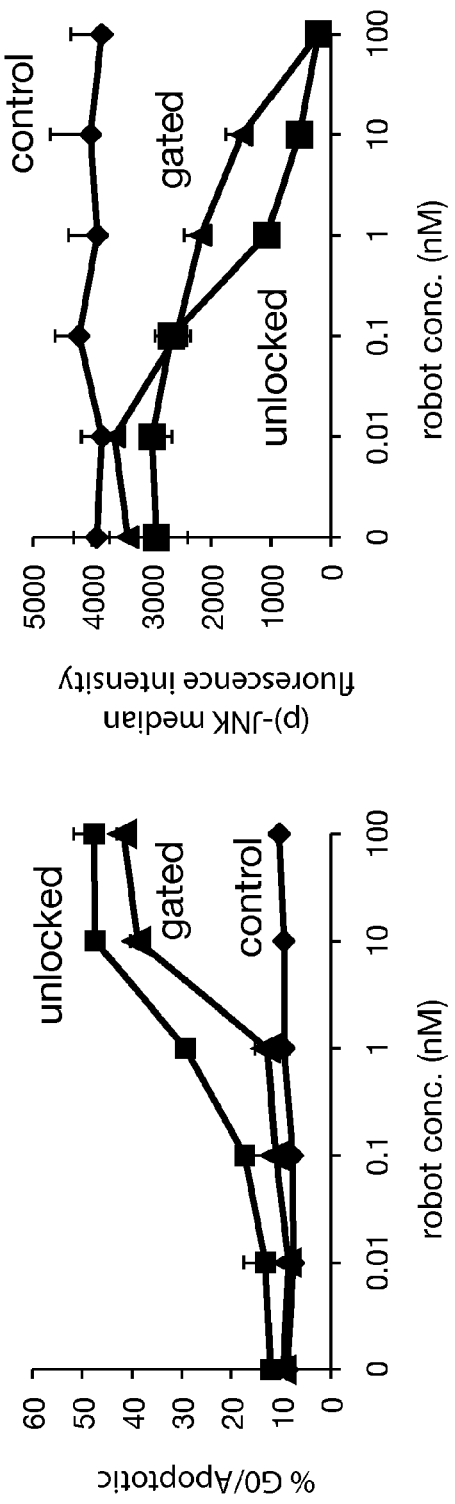
FIG. 5A
FIG. 5B
FIG. 5C

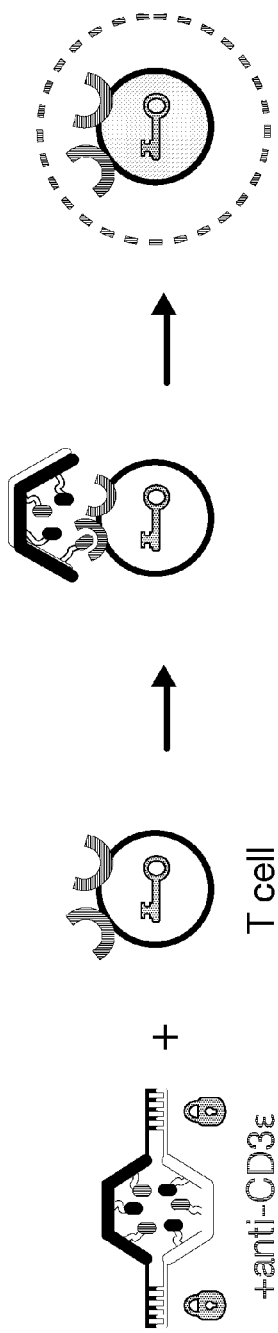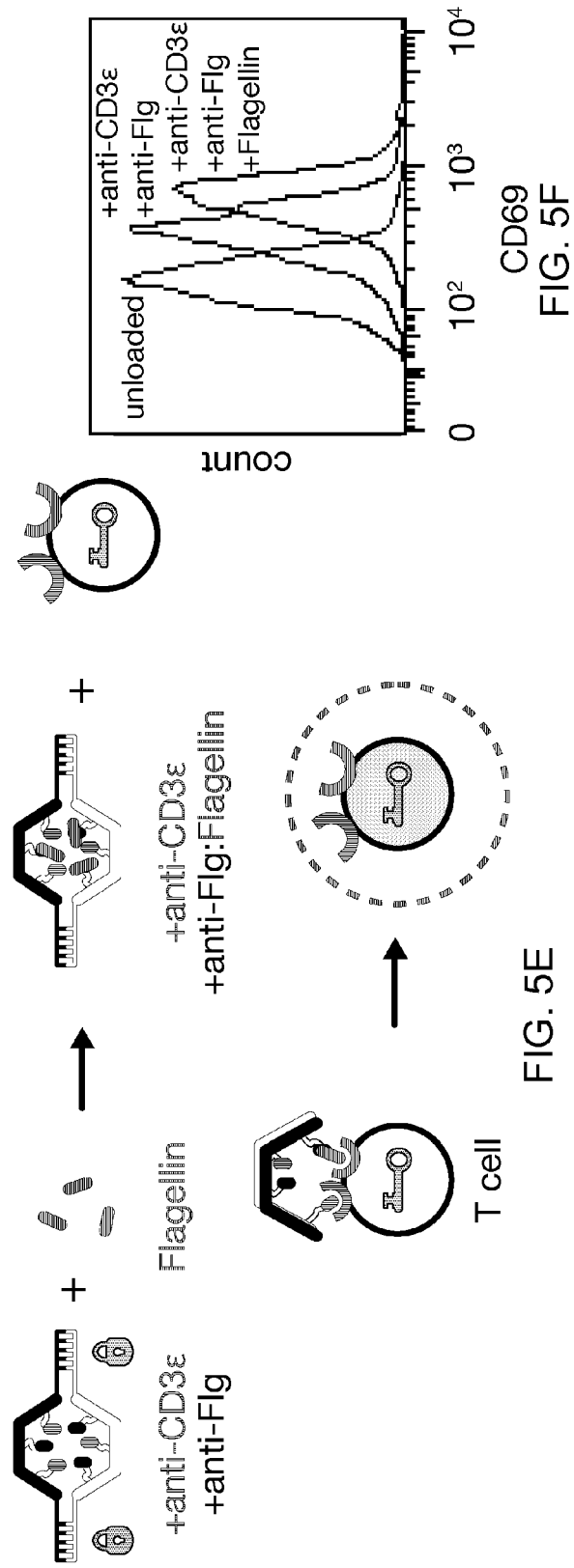
FIG. 5D
FIG. 5E
FIG. 5F

SEQUENCE LISTING

```
<160> NUMBER OF SEQ ID NOS: 234

<210> SEQ ID NO 1
<211> LENGTH: 7308
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
aatgctacta ctattagtag aattgatgcc accttttcag ctcgcgcccc aaatgaaaat      60
atagctaaac aggttattga ccatttgcga aatgtatcta atggtcaaac taaatctact     120
cgttcgcaga attgggaatc aactgttata tggaatgaaa cttccagaca ccgtactta     180 gttgcatatt taaaacatgt tgagctacag cattatattc agcaattaag ctctaagcca     240
tccgcaaaaa tgacctctta tcaaaggag caattaaagg tactctctaa tcctgacctg     300
ttggagtttg cttccggtct ggttcgcttt gaagctcgaa ttaaaacgcg atatttgaag    360
tctttcgggc ttcctcttaa tcttttgat gcaatccgct ttgcttctga ctataatagt     420
cagggtaaag acctgatttt tgatttatgg tcattctcgt tttctgaact gtttaaagca    480 tttgagggg attcaatgaa tatttatgac gattccgcag tattggacgc tatccagtct     540
aaacatttta ctattacccc ctctggcaaa acttcttttg caaaagcctc tcgctatttt    600
ggtttttatc gtcgtctggt aaacgagggt tatgatagtg ttgctcttac tatgcctcgt    660
aattcctttt ggcgttatgt atctgcatta gttgaatgtg gtattcctaa atctcaactg    720
atgaatcttt ctacctgtaa taatgttgtt ccgttagttc gttttattaa cgtagatttt    780
tcttcccaac gtcctgactg gtataatgag ccagttctta aaatcgcata aggtaattca    840
caatgattaa agttgaaatt aaaccatctc aagcccaatt tactactcgt tctggtgttt   900
ctcgtcaggg caagccttat tcactgaatg agcagcttt ttacgttgat ttgggtaatg     960
aatatccggt tcttgtcaag attactcttg atgaaggtca gccagcctat gcgcctggtc   1020
tgtacaccgt tcatctgtcc tctttcaaag ttggtcagtt cggttccctt atgattgacc   1080
gtctgcgcct cgttccggct aagtaacatg gagcaggtcg cggatttcga cacaatttat   1140
caggcgatga tacaaatctc cgttgtactt tgtttcgcgc ttggtataat cgctgggggt    1200
caaagatgag tgttttagtg tattcttttg cctctttcgt tttaggttgg tgccttcgta   1260
gtggcattac gtattttacc cgtttaatgg aaacttcctc atgaaaaagt ctttagtcct   1320
caaagcctct gtagccgttg ctaccctcgt tccgatgctg tctttcgctg ctgagggtga   1380
cgatcccgca aaagcggcct ttaactccct gcaagcctca gcgaccgaat atatcggtta    1440
tgcgtgggcg atggttgttg tcattgtcgg cgcaactatc ggtatcaagc tgtttaagaa    1500
```

```
attcacctcg aaagcaagct gataaaccga tacaattaaa ggctccttTt ggagccttTT      1560
ttTTggagat tTTcaacgtg aaaaaattat tattcgcaat tccttTagTT gttccttTct      1620
attctcactc cgctgaaact gTTgaaagTT gtTTagcaaa atcccataca gaaaattcat      1680
ttactaacgt ctggaaagac gacaaaactt tagatcgtta cgctaactat gagggctgtc      1740
tgtggaatgc tacaggcgtt gtagtttgta ctggtgacga aactcagtgt tacggtacat      1800
gggttcctat tgggcttgct atccctgaaa atgagggtgg tggctctgag ggtgcggtt      1860 ctgagggtgg cggttctgag ggtggcggta ctaaacctcc tgagtacggt gatacaccta      1920
ttccgggcta tacttatatc aaccctctcg acggcactta tccgcctggt actgagcaaa      1980
accccgctaa tcctaatcct tctcttgagg agtctcagcc tcttaatact ttcatgtttc      2040
agaataatag gttccgaaat aggcagggg cattaactgt ttatacgggc actgttactc      2100
aaggcactga ccccgttaaa acttattacc agtacactcc tgtatcatca aaagccatgt      2160
atgacgctta ctggaacggt aaattcagag actgcgcttt ccattctggc tttaatgagg      2220
atttatttgt ttgtgaatat caaggccaat cgtctgaccc gcctcaacct cctgtcaatg      2280
ctggcggcgg ctctggtggt ggttctggtg gcggctctga gggtggtggc tctgagggtg      2340
gcggttctga gggtggcggc tctgaggag gcggttccgg tggtggctct ggttccggtg      2400
attttgatta tgaaaagatg gcaaacgcta ataagggggc tatgaccgaa atgccgatg      2460 aaaacgcgct acagtctgac gctaaaggca aacttgattc tgtcgctact gattacggtg      2520
ctgctatcga tggtttcatt ggtgacgttt ccggccttgc taatggtaat ggtgctactg      2580 gtgatttgc tggctctaat cccaaatgg ctcaagtcgg tgacggtgat aattcacctt      2640
taatgaataa tttccgtcaa tatttacctt ccctccctca atcggttgaa tgtcgccctt      2700
ttgtctttgg cgctggtaaa ccatatgaat tttctattga ttgtgacaaa ataaacttat      2760
tccgtggtgt ctttgcgttt cttttatatg ttgccacctt tatgtatgta ttttctacgt      2820
ttgctaacat actgcgtaat aaggagtctt aatcatgcca gttcttttgg gtattccgtt      2880
attattgcgt ttcctcggtt tccttctggt aactttgttc ggctatctgc ttactttTct      2940
taaaaagggc ttcggtaaga tagctattgc tatttcattg tttcttgctc ttattattgg      3000
gcttaactca attcttgtgg ttatctctc tgatattagc gctcaattac cctctgactt      3060
tgttcagggt gttcagttaa ttctcccgtc taatgcgctt ccctgttttt atgttattct      3120
ctctgtaaag gctgctattt tcattttga cgttaaacaa aaaatcgttt cttatttgga      3180
ttgggataaa taatatggct gtttatttTg taactggcaa attaggctct ggaaagacgc      3240
tcgttagcgt tggtaagatt caggataaaa ttgtagctgg gtgcaaaata gcaactaatc      3300
ttgatttaag gcttcaaaac ctcccgcaag tcgggaggtt cgctaaaacg cctcgcgttc      3360
ttagaatacc ggataagcct tctatatctg atttgcttgc tattgggcgc ggtaatgatt      3420
cctacgatga aaataaaaac ggcttgcttg ttctcgatga gtgcggtact tggtttaata      3480
cccgttcttg gaatgataag gaaagacagc cgattattga ttggttTcta catgctcgta      3540
aattaggatg ggatattatt ttTcttgttc aggacttatc tattgttgat aaacaggcgc      3600
gTTctgcatt agctgaacat gTTgtTTatt gtcgtcgtct ggacagaatt actTTacctt      3660
ttgtcggtac tttatattct cttattactg gctcgaaaat gcctctgcct aaattacatg      3720
ttggcgttgt taaatatggc gattctcaat taagccctac tgttgagcgt tggctttata      3780
ctggtaagaa tTTgtataac gcatatgata ctaaacaggc tttTTctagt aattatgatt      3840
ccggtgttta ttcttatttta acgccttatt tatcacacgg tcggtatttc aaaccattaa      3900
```

```
atttaggtca gaagatgaaa ttaactaaaa tatatttgaa aaagttttct cgcgttcttt      3960
gtcttgcgat tggatttgca tcagcattta catatagtta tataacccaa cctaagccgg      4020
aggttaaaaa ggtagtctct cagacctatg attttgataa attcactatt gactcttctc      4080
agcgtcttaa tctaagctat cgctatgttt tcaaggattc taagggaaaa ttaattaata      4140
gcgacgattt acagaagcaa ggttattcac tcacatatat tgatttatgt actgtttcca      4200
ttaaaaaagg taattcaaat gaaattgtta aatgtaatta attttgtttt cttgatgttt      4260
gtttcatcat cttcttttgc tcaggtaatt gaaatgaata attcgcctct gcgcgatttt      4320
gtaacttggt attcaaagca atcaggcgaa tccgttattg tttctcccga tgtaaaaggt      4380
actgttactg tatattcatc tgacgttaaa cctgaaaatc tacgcaattt ctttatttct      4440
gttttacgtg caaataattt tgatatggta ggttctaacc cttccattat tcagaagtat      4500
aatccaaaca atcaggatta tattgatgaa ttgccatcat ctgataatca ggaatatgat      4560
gataattccg ctccttctgg tggtttcttt gttccgcaaa atgataatgt tactcaaact      4620
tttaaaatta ataacgttcg ggcaaaggat ttaatacgag ttgtcgaatt gtttgtaaag      4680
tctaatactt ctaaatcctc aaatgtatta tctattgacg gctctaatct attagttgtt      4740
agtgctccta agatattttt agataacctt cctcaattcc tttcaactgt tgatttgcca      4800
actgaccaga tattgattga gggttttgata tttgaggttc agcaaggtga tgctttagat      4860
ttttcatttg ctgctggctc tcagcgtggc actgttgcag gcggtgttaa tactgaccgc      4920
ctcacctctg ttttatcttc tgctggtggt tcgttcggta tttttaatgg cgatgtttta      4980
gggctatcag ttcgcgcatt aaagactaat agccattcaa aaatattgtc tgtgccacgt      5040
attcttacgc tttcaggtca aaggggttct atctctgttg gccagaatgt ccctttttatt     5100 actggtcgtg tgactggtga atctgccaat gtaaataatc catttcagac gattgagcgt      5160
caaaatgtag gtatttccat gagcgttttt cctgttgcaa tggctggcgg taatattgtt      5220
ctggatatta ccagcaaggc cgatagtttg agttcttcta ctcaggcaag tgatgttatt      5280
actaatcaaa gaagtattgc tacaacggtt aatttgcgtg atggacagac tcttttactc      5340
ggtggcctca ctgattataa aaacacttct caggattctg cgtaccgttc ctgtctaaa      5400 atcccttttaa tcggcctcct gtttagctcc cgctctgatt ctaacgagga agcacgttta      5460
tacgtgctcg tcaaagcaac catagtacgc gccctgtagc ggcgcattaa gcgcggcggg      5520
tgtggtggtt acgcgcagcg tgaccgctac acttgccagc gccctagcgc ccgctccttt      5580
cgctttcttc ccttcctttc tcgccacgtt cgccggcttt ccccgtcaag ctctaaatcg      5640
ggggctccct ttagggttcc gatttagtgc tttacggcac ctcgacccca aaaaacttga      5700
tttgggtgat ggttcacgta gtgggccatc gccctgatag acggtttttc gccctttgac      5760
gttggagtcc acgttcttta atagtggact cttgttccaa actggaacaa cactcaaccc      5820
tatctcgggc tattcttttg atttataagg gattttgccg atttcggaac caccatcaaa      5880
caggattttc gcctgctggg gcaaaccagc gtggaccgct tgctgcaact ctctcagggc      5940
caggcggtga agggcaatca gctgttgccc gtctcactgg tgaaaagaaa aaccaccctg      6000
gcgcccaata cgcaaaccgc ctctccccgc gcgttggccg attcattaat gcagctggca      6060
cgacaggttt cccgactgga aagcgggcag tgagcgcaac gcaattaatg tgagttagct      6120
cactcattag gcaccccagg ctttacactt tatgcttccg gctcgtatgt tgtgtggaat      6180
tgtgagcgga taacaatttc acacaggaaa cagctatgac catgattacg aattcgagct      6240
```

```
cggtacccgg ggatccttat acgggtacta gccatgcgta tacggtcgct agcggacttg     6300
cctcgctatc aaaggtctag agtcgacctg caggcatgca agcttggcac tggccgtcgt     6360
tttacaacgt cgtgactggg aaaaccctgg cgttacccaa cttaatcgcc ttgcagcaca     6420
tccccctttc gccagctggc gtaatagcga agaggcccgc accgatcgcc cttcccaaca     6480
gttgcgcagc ctgaatggcg aatggcgctt tgcctggttt ccggcaccag aagcggtgcc     6540
ggaaagctgg ctggagtgcg atcttcctga ggccgatact gtcgtcgtcc cctcaaactg     6600
gcagatgcac ggttacgatg cgcccatcta caccaacgtg acctatccca ttacggtcaa     6660
tccgccgttt gttcccacgg agaatccgac gggttgttac tcgctcacat ttaatgttga     6720
tgaaagctgg ctacaggaag gccagacgcg aattatttt gatggcgttc ctattggtta      6780
aaaaatgagc tgatttaaca aaaatttaat gcgaatttta acaaaatatt aacgtttaca     6840
atttaaatat ttgcttatac aatcttcctg tttttggggc ttttctgatt atcaaccggg     6900
gtacatatga ttgacatgct agttttacga ttaccgttca tcgattctct tgtttgctcc     6960
agactctcag gcaatgacct gatagccttt gtagatctct caaaaatagc taccctctcc     7020
ggcattaatt tatcagctag aacggttgaa tatcatattg atggtgattt gactgtctcc     7080
ggcctttctc accctttga atctttacct acacattact caggcattgc atttaaaata     7140
tatgagggtt ctaaaattt ttatccttgc gttgaaataa aggcttctcc cgcaaaagta     7200
ttacagggtc ataatgtttt tggtacaacc gatttagctt tatgctctga ggctttattg     7260
cttaattttg ctaattcttt gccttgcctg tatgatttat tggatgtt                 7308

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tttagttaat ttcaattaat tttccctttg agtga                               35

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
agaaaacttt ttcattgaaa acatagcg                                       28

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
aatcgcaaga caaaagatta agacgctg                                       28

<210> SEQ ID NO 5
<211> LENGTH: 42
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 5
gttatattca taggtctgag acatcaagaa aacaaatttc aa                          42

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tgaattttac atttaacaat ttcgcgca                                          28

<210> SEQ ID NO 7
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ataacctcct tttacatcgg gtttcaggtt taacgaaaag tt                          42

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
acaatatatg agaatccaat atat                                              24

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
attcgccaaa taaagaaatt gattttgc                                          28

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tgcatggaaa atagcttgaa cgcg                                              24

<210> SEQ ID NO 11
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 11
aaatcatttg agaagagcaa atcc                                              24

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gaggcgaggt tagaacctac catcatat                                          28

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ttacctgtat acttctgaat atgatggc                                          28

<210> SEQ ID NO 14
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tgagtaaact cgtattaaat ccagagatac atcgccatta                             40

<210> SEQ ID NO 15
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ggaacaagac tttacaaaca actgaaaggc gcgaaagata aa                          42

<210> SEQ ID NO 16
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ggagcggttt gaggatttag agcacagaca ataatctcaa tc                          42

<210> SEQ ID NO 17
<211> LENGTH: 42
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 17
tcctgatgag ccgtcaatag acagttggat caaacaacag tg                          42

<210> SEQ ID NO 18
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
aattcatgca ctaacaacta aaaggaatc accttagcag ca                           42

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
taaagcattg aggatgcaac aggaaaaatt gc                                     32

<210> SEQ ID NO 20
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
aaaataccga acgaaccacc agtgagaatt aaccgttgta attc                        44

<210> SEQ ID NO 21
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
agactgatag ccctaaaaga acccagtcac a                                      31

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
acagaggcct gagattcttt gattagtaat gg                                     32

<210> SEQ ID NO 23
<211> LENGTH: 31
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 23
gcgtattagt ctttaatcgt aagaatttac a                          31

<210> SEQ ID NO 24
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ttaacacaca ggaacacttg cctgagtatt tg                         32

<210> SEQ ID NO 25
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ccacgctggc cgattcaaac tatcggcccg ct                         32

<210> SEQ ID NO 26
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gccgctgaac ctcaaatcaa atcaggaaat a                          31

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
aatgaaacag agcgtaatat c                                     21

<210> SEQ ID NO 28
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
cgaccagtca cgcagccacc gctggcaaag cgaaagaac                  39

<210> SEQ ID NO 29
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
accttctgac ttcgacacat tatccgtaga tagaa					35

<210> SEQ ID NO 30
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ttggcaggca atacagtgtt tctgcgcggg cg					32

<210> SEQ ID NO 31
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
attatacgtg agtattaaga aaccaaaaca gtgat					35

<210> SEQ ID NO 32
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gtctgaaata acatcggtac ggccgcgcac gg					32

<210> SEQ ID NO 33
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
acgatctggt taatacaaat tatcatatca ataca					35

<210> SEQ ID NO 34
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
cctacatgaa gaactaaagg gcagggcgga gccccgggc					39

<210> SEQ ID NO 35
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
catacagttg tagattatat cagaatggaa gatta                                      35

<210> SEQ ID NO 36
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
tggggagcta tttgacgact aaataccatc agttt                                      35

<210> SEQ ID NO 37
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ggaagaagtg tagcggtcac gttataatca gc                                         32

<210> SEQ ID NO 38
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
agagaacgtg aatcaaatgc gtatttccag tcccc                                      35

<210> SEQ ID NO 39
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
cgaacgttaa ccaccacacc cccagaattg ag                                         32

<210> SEQ ID NO 40
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ggaagggcga aaatcgggtt tttcgcgttg ctcgt                                      35

<210> SEQ ID NO 41
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gagcttgtta atgcgccgct aattttagcg cctgccctca at        42

<210> SEQ ID NO 42
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ctaaaggcgt actatggttg caacaggaga ga        32

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gccgtaaagc agcacgtata a        21

<210> SEQ ID NO 44
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
aagtagggtt aacgcgctgc cagcggctag tagtccgc        38

<210> SEQ ID NO 45
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gattcctgtt acgggcagtg agcttttcct gaacgacg        38

<210> SEQ ID NO 46
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gccttcaccg aaagcctccg ctcattccca g        31

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47

```
gtccacgctg cccaaatcaa g                                              21
```

<210> SEQ ID NO 48
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48

```
ggcggttaga atagcccgag aagtccacta ttaaaaagga ag                       42
```

<210> SEQ ID NO 49
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49

```
cagggtgcaa aatcccttat agactccaac gtcaaaagcc gg                       42
```

<210> SEQ ID NO 50
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50

```
cagtgagtga tggtggttcc gaaaaccgtc tatcacgatt ta                       42
```

<210> SEQ ID NO 51
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51

```
attgccccca gcaggcgaaa aggcccacta cgtgacggaa cc                       42
```

<210> SEQ ID NO 52
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52

```
aaatgccagt ttgaggggga ttgagtgagc gaatagga                            38
```

<210> SEQ ID NO 53
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53

```
gggtagacct ttgatagatt aaatccgtaa t                                   31
```

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ctcgaatgct cactacagta t                                              21

<210> SEQ ID NO 55
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
aattgcatgc ctgcaggacc cgtcggattt caaatcag                            38

<210> SEQ ID NO 56
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
gctcatggtc atagctgaac tcactcgcac t                                   31

<210> SEQ ID NO 57
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
taatgtgaaa ttgttatggg gtgcggcacc g                                   31

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
tcacgactgt gctggcgcaa c                                              21

<210> SEQ ID NO 59
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
aacgccaggg ttcaattcca cacaacatac g                                   31

<210> SEQ ID NO 60
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
gggataggtg catccctgtc gggggaga                                          28

<210> SEQ ID NO 61
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
aaacggcgac gacggcccgc ttgggcgc                                          28

<210> SEQ ID NO 62
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
cgggcctagg aagaattaat tttttcac                                          28

<210> SEQ ID NO 63
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
tgttggggct ttccctaatg aacagctg                                          28

<210> SEQ ID NO 64
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
tcgccattgc cggaaaagtg tcctggcc                                          28

<210> SEQ ID NO 65
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
cgtaaccgtc acgtcagctt taattcgc                                          28

```
<210> SEQ ID NO 66
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
ccagccaaag ggcgtggcga aaattcgc                                         28

<210> SEQ ID NO 67
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
cttctggtca ggctcaaggc gtaaacgt                                         28

<210> SEQ ID NO 68
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
aatcatcaac cgaggcaacc cgtataagga tcggg                                 35

<210> SEQ ID NO 69
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
acgccatgaa cggtaatcgt agagatctac aaaggtaaaa at                         42

<210> SEQ ID NO 70
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
ctcatttcat gtcaatcata tggagagggt agctatatat tt                         42

<210> SEQ ID NO 71
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
attaaatggt tgataatcag atctagctga taaatgagta at                         42

<210> SEQ ID NO 72
```

<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
taatattcaa aaacaggaag aatcaatatg atatttcaaa ag       42

<210> SEQ ID NO 73
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
atatttaaat tgattaagtt gggt       24

<210> SEQ ID NO 74
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
acaagaggtc attgcctgag agcctttatt tcaacaatac tt       42

<210> SEQ ID NO 75
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
tgaaaactag tttaaccagt aacatcgact ctaccgag       38

<210> SEQ ID NO 76
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
gccgtacccc ttttgttgct attaccaa       28

<210> SEQ ID NO 77
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
ttttagacca aaaacattat gcaataac       28

<210> SEQ ID NO 78
<211> LENGTH: 35

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
taaatgccat aaagctaaat ctttcatttg gggcg                              35

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
ggtgagacaa ggcaaagaat t                                             21

<210> SEQ ID NO 80
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
agcaaaataa agatcaaccg taaagccctt gttaaagggg gagttg                  46

<210> SEQ ID NO 81
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
atttcgcaaa tggtaccctg tgcaaggact atcagaatcg atcaaa                  46

<210> SEQ ID NO 82
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
ctgtttagct atatggttgt aaccctcatt tt                                 32

<210> SEQ ID NO 83
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
cgagctgctc agagaatgcc ttaat                                         25

<210> SEQ ID NO 84
<211> LENGTH: 32
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 84
tagatttagt ttgaaaccag agcgttttag gg                          32

<210> SEQ ID NO 85
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
ccatatatac ctttcatcaa actgcggacc ct                          32

<210> SEQ ID NO 86
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
ttttaaatgg cttaggtctt tctttaaaca aa                          32

<210> SEQ ID NO 87
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
agggcccgaa tagactgtaa aaacaaatct atcat                       35

<210> SEQ ID NO 88
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
tagagagaca gttgattccc aattctgcca ac                          32

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89 cctttttgctg gaagtttcat t                                     21

<210> SEQ ID NO 90
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 90
tcaaaaatca gagcttaatt g                                              21

<210> SEQ ID NO 91
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
ggtgcttttg cagtcaggat tttaacag                                       28

<210> SEQ ID NO 92
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
aaatgttaga cttcaaatat cccggaagca aactcgaacg ag                       42

<210> SEQ ID NO 93
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
tgagtaagag caggtaggag tagtcaagaa caatc                               35

<210> SEQ ID NO 94
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
acgacgagat agcgtccaat aaagattaag aggaatcagg at                       42

<210> SEQ ID NO 95
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
cgtactaacg atggtttctt catctactta ggagg                               35

<210> SEQ ID NO 96
<211> LENGTH: 42
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 96
atcataaatc gtcataaata tagcaaagcg gattgaattg ct                              42

<210> SEQ ID NO 97
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
aggcataatc cccctcaaat gaccctgact attatgtcat tt                              42

<210> SEQ ID NO 98
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
aggtgagatt cctgacgcca aatctcgcct gcgat                                     35

<210> SEQ ID NO 99
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
tacataacgc cagttcagaa a                                                    21

<210> SEQ ID NO 100
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
cttatgcgac gttgggaaga acaaaatagc gagagaatag ta                              42

<210> SEQ ID NO 101
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
tgtcaggcgc agacggtagg cacctgagga c                                         31

<210> SEQ ID NO 102
<211> LENGTH: 28
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 102
actttaacgt taataaaacg attaccag                28

<210> SEQ ID NO 103
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
gcttgaggaa caacattatt acaacact                28

<210> SEQ ID NO 104
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
ccagaacaaa gattcatcag taattacg                28

<210> SEQ ID NO 105
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
ggcttgctag gaatacca                18

<210> SEQ ID NO 106
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
atgccgaact aaatacgtga ggaa                24

<210> SEQ ID NO 107
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
cgcacactca agacagcat cggaatatga caacaacc                38

<210> SEQ ID NO 108
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 108
aacgaaaccg aacttttc acgttgaagg ga                32

<210> SEQ ID NO 109
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
caatagcaac ggctacattt ccagtgctaa a                31

<210> SEQ ID NO 110
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
cactaaagac ctgcaaaaaa aaggctccgt tgcgcc            36

<210> SEQ ID NO 111
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
cccccagata aattgccttt aattgtattt aa               32

<210> SEQ ID NO 112
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
tatgatcgtc accctcaacg catagcttga taccgataaa aa     42

<210> SEQ ID NO 113
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
tcataatgcc actacgacaa tcataaagga attgcgaaca ac     42

<210> SEQ ID NO 114
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
taaagacacg atctttcagc ggagtgag					28

<210> SEQ ID NO 115
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
ggccgcttcg ctgatcgagg tgaatttccg gtttatgtat caaacgtaa					49

<210> SEQ ID NO 116
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
agtaaagttt tcaccagtac aaacggataa g					31

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
caacttttaa taatgaggcg c					21

<210> SEQ ID NO 118
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
gacatttctg tataatctcc tccatgt					27

<210> SEQ ID NO 119
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
acaaccgata ccaccctcat tttcggaggt t					31

<210> SEQ ID NO 120
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
aaaggaacaa ctaagggaaa acggtgtaca gacgaattac                                    40

<210> SEQ ID NO 121
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
ggagtgtcga cggatattca ttacagaaac a                                              31

<210> SEQ ID NO 122
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
cattaaatga acgagggaag aata                                                      24

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
gaaccgccac cctctcagaa c                                                         21

<210> SEQ ID NO 124
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
tgccgtcaga ggctgagact cccagaatgg aaagcggttg ag                                  42

<210> SEQ ID NO 125
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
gggagtttcg tgtcgtcgag gcttaaccta a                                              31

<210> SEQ ID NO 126
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
aagtatattc tgaaacatga actgaattta ccgttccgcc gccag        45

<210> SEQ ID NO 127
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
tatcacctgc ctatttcgga agcgtcatac atggcccacc ag        42

<210> SEQ ID NO 128
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
tcaagggata atcgcccgca gcgatctttg a        31

<210> SEQ ID NO 129
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
tagtaccgta taaacagtta agatacagga gtgtagagcc ac        42

<210> SEQ ID NO 130
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
cccagagcca tattcggttt gcggaccaag c        31

<210> SEQ ID NO 131
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
aagctcaaga accaggctac aacgtagcgt atttt        35

<210> SEQ ID NO 132
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
gcaggtcaac cgatttggga aaccatta        28

```
<210> SEQ ID NO 133
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
aaccacccaa taatcaaaat ctataaaa                                           28

<210> SEQ ID NO 134
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
caccctccca gagcccctta tgacagaa                                           28

<210> SEQ ID NO 135
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
aaccgcccct cccttcggca tagcgtca                                           28

<210> SEQ ID NO 136
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
attaccagag ccagtaacct attagcccgg aaacc                                   35

<210> SEQ ID NO 137
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
gcaaggcgaa acaatagccg aacaaagtta tt                                      32

<210> SEQ ID NO 138
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
aacccgactt gagccattga gggatcacaa t                                       31
```

<210> SEQ ID NO 139
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
atgaaactaa gcccaggaaa ccgaggaaaa agacaaatt                              39

<210> SEQ ID NO 140
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
gataaaggtg aattatctga cggaccacgg a                                      31

<210> SEQ ID NO 141
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
ccgtaatgat aaccaataac ggaataccgg ca                                     32

<210> SEQ ID NO 142
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
tcaagttatt gagcactggc atgattaaag aa                                     32

<210> SEQ ID NO 143
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143 tttttcggt catagcccac caccacatac ataaaggtca aaagagcta                    49

<210> SEQ ID NO 144
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
caatagaaag cagatgaaat aaaacgatag tt                                     32

<210> SEQ ID NO 145
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 145
ttggggaagg gacaggagca gtctagtatt agaga                          35

<210> SEQ ID NO 146
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 146
ataagtttac cagaaataat acaaaaatct tt                             32

<210> SEQ ID NO 147
<211> LENGTH: 46
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 147
gaaacgcacg caatcacaag attacagact taccattcta agcatt              46

<210> SEQ ID NO 148
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 148
acaaccggaa agagccgttt tgattgcccc cgtac                          35

<210> SEQ ID NO 149
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 149
aatggaaccg accctcactg gtaaagtgcc cgcca                          35

<210> SEQ ID NO 150
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 150
caaacgtgac tcctaaagtc aggagaatat ta                             32

<210> SEQ ID NO 151

<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
gaaaagtaaa ttcagacatt cagacgatat ta                                32

<210> SEQ ID NO 152
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
ataaacaggg agctacatag cgaataatcg gatagata                          38

<210> SEQ ID NO 153
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
aaataaggca atagcaccat tttagagcca gcaaaaaagg gctatggtt              49

<210> SEQ ID NO 154
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
acagcccaat gaacaagctg tccaccagta accgaccg                          38

<210> SEQ ID NO 155
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
atttgccttt ttgtttaacg tagagcaacg ga                                32

<210> SEQ ID NO 156
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
ccaatataga accaagtaca acatttaggc acgttaaa                          38

<210> SEQ ID NO 157
<211> LENGTH: 32

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
cgagcgtgaa aatagcagcc tattgagtca tc                                    32

<210> SEQ ID NO 158
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
cctgaatgag aataacataa atcagagaca gtagctagcg tt                         42

<210> SEQ ID NO 159
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
tgcacccaag cgcattagac ggagggtatg cc                                    32

<210> SEQ ID NO 160
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
gttggaggtt gagcatgaaa ataa                                             24

<210> SEQ ID NO 161
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
atcattaccg caaataaaca gc                                               22

<210> SEQ ID NO 162
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
tcatcgaagc aagcaaatca ggagccta                                         28

<210> SEQ ID NO 163
<211> LENGTH: 28
<212> TYPE: DNA

<213> ORGANISM: Artificial Sequence
<220> FEATURE:
<223> OTHER INFORMATION: Description of Artificial Sequence: Synthetic oligonucleotide

<400> SEQUENCE: 163
gtattaaagg cttatccggt aacgctaa                                28

<210> SEQ ID NO 164
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 164
ccagaacgcg ttaacaagga atca                                    24

<210> SEQ ID NO 165
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 165
tccttataac gcgaggcgtt tattttat                                28

<210> SEQ ID NO 166
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 166
caatcaacct cccgacttgc ggctattt                                28

<210> SEQ ID NO 167
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 167
aaggtaaagt aattcaagcc g                                       21

<210> SEQ ID NO 168
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 168
tttcgaggac gacgacaata aaccgcac                                28

<210> SEQ ID NO 169
<211> LENGTH: 28
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 169
atgtaatgtt cagctaatgc aagaacgg                                            28

<210> SEQ ID NO 170
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
gccatatcct gtttatcaac actgtctt                                            28

<210> SEQ ID NO 171
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
agtagggagt cctgaacaag atagaaac                                            28

<210> SEQ ID NO 172
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
ggtttgaaat ataagagaat at                                                  22

<210> SEQ ID NO 173
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
tgtgataaat aagggaggca t                                                   21

<210> SEQ ID NO 174
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
taagaataaa cacccgccaa c                                                   21

<210> SEQ ID NO 175
<211> LENGTH: 21
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 175
taattactag aaaagagaat c                                            21

<210> SEQ ID NO 176
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
ttcaattaat atcaaaaaac tata                                         24

<210> SEQ ID NO 177
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
ttagtatcat atgcgctcaa c                                            21

<210> SEQ ID NO 178
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
ctaaagtacg gtgtataaga gagtcagatc at                                32

<210> SEQ ID NO 179
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
gtgtaggtta agcaataaag caaaaggtgg catca                             35

<210> SEQ ID NO 180
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
cagtacataa atcaataacg gttgtgctac tccagttc                          38

<210> SEQ ID NO 181
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 181
aattaccttt tttatttgaa tttgtgctac tccagttc					38

<210> SEQ ID NO 182
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182 cattttgaa tggcgtcagt attgtgctac tccagttc					38

<210> SEQ ID NO 183
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
gccagtgcgc cagcatcggt gttgtgctac tccagttc					38

<210> SEQ ID NO 184
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
cggcctcctc tccgtgggaa cttgtgctac tccagttc					38

<210> SEQ ID NO 185
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
ataggctggc tgacaatttc attgtgctac tccagttc					38

<210> SEQ ID NO 186
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
aagagtaatc ttgaaaattg gttgtgctac tccagttc					38

<210> SEQ ID NO 187
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
gcaagcccaa taggataggt gttgtgctac tccagttc                    38

<210> SEQ ID NO 188
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
catttaaata taccgtcagt caccattgtg ctactccagt tc                42

<210> SEQ ID NO 189
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
tgccatcttt tcttagcagc attgtgctac tccagttc                    38

<210> SEQ ID NO 190
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
accaagtaat tatttgcacg taccagaatt gtgctactcc agttc             45

<210> SEQ ID NO 191
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
tttacgttag gtaccgtaac actgttgata tttgtgctac tccagttc          48

<210> SEQ ID NO 192
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
cttaattagc ctgttgtaaa tgctgatgtc aatagcatca tgg               43

<210> SEQ ID NO 193
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
ttgcggatat gcaaattcta ctaatagtgc tgacgt                                    36

<210> SEQ ID NO 194
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
ccaacgttat acaaattctt atactcaggg cactgcaagc aattgtggtc ccaatgggct          60
gagta                                                                     65

<210> SEQ ID NO 195
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
agtagcatta acatccaatt actcagggca ctgcaagcaa ttgtggtccc aatgggctga         60
gta                                                                       63

<210> SEQ ID NO 196
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
tactcagccc attgggacca caattgcttg cagtgccctg agtaaacctc cggcttaggt         60
tgg                                                                       63

<210> SEQ ID NO 197
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
tactcagccc attgggacca caattgcttg cagtgccctg agtaaatgct gtagctcaac         60
atg                                                                       63

<210> SEQ ID NO 198
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
agtagcatta acatccaatt aacagggtcg cccatcggtt cgaatcagac ggtttaaggc         60
agt                                                                       63

<210> SEQ ID NO 199
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
ccaacgttat acaaattctt ataacagggt cgcccatcgg ttcgaatcag acggtttaag    60
gcagt                                                                65

<210> SEQ ID NO 200
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
actgccttaa accgtctgat tcgaaccgat gggcgaccct gttaaatgct gtagctcaac    60
atg                                                                  63

<210> SEQ ID NO 201
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
actgccttaa accgtctgat tcgaaccgat gggcgaccct gttaaacctc cggcttaggt    60
tgg                                                                  63

<210> SEQ ID NO 202
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
ccaacgttat acaaattctt aaccaaacac agatgcaacc tgacttctaa cgtcatttgg    60
tg                                                                   62

<210> SEQ ID NO 203
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
caccaaatga cgttagaagt caggttgcat ctgtgtttgg taacctccgg cttaggttgg    60

<210> SEQ ID NO 204
<211> LENGTH: 60
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 204
agtagcatta acatccaata ccaaacacag atgcaacctg acttctaacg tcatttggtg    60

<210> SEQ ID NO 205
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
caccaaatga cgttagaagt caggttgcat ctgtgtttgg taatgctgta gctcaacatg    60

<210> SEQ ID NO 206
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
ccaacgttat acaaattctt aaacaccgtg gaggatagtt cggtggctgt tcagggtctc    60
ctcccggtg                                                            69

<210> SEQ ID NO 207
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
caccgggagg agaccctgaa cagccaccga actatcctcc acggtgttaa cctccggctt    60
aggttgg                                                              67

<210> SEQ ID NO 208
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
agtagcatta acatccaata acaccgtgga ggatagttcg gtggctgttc agggtctcct    60
cccggtg                                                              67

<210> SEQ ID NO 209
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
caccgggagg agaccctgaa cagccaccga actatcctcc acggtgttaa tgctgtagct    60
caacatg                                                              67

<210> SEQ ID NO 210
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
ccaacgttat acaaattctt aaggccccca ggctcggtgg atgcaaacac atgactatgg      60
gcccgt                                                                66

<210> SEQ ID NO 211
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
acgggcccat agtcatgtgt ttgcatccac cgagcctggg ggcctaacct ccggcttagg      60
ttgg                                                                  64

<210> SEQ ID NO 212
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
agtagcatta acatccaata ggcccccagg ctcggtggat gcaaacacat gactatgggc      60
ccgt                                                                  64

<210> SEQ ID NO 213
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
acgggcccat agtcatgtgt ttgcatccac cgagcctggg ggcctaatgc tgtagctcaa      60
catg                                                                  64

<210> SEQ ID NO 214
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
ccaacgttat acaaattctt acagctacgc aatacaaaac tccgaacacc tgcttctgac      60
tgggtgctg                                                             69

<210> SEQ ID NO 215
<211> LENGTH: 67

-continued

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
cagcacccag tcagaagcag gtgttcggag ttttgtattg cgtagctgaa cctccggctt    60
aggttgg                                                              67

<210> SEQ ID NO 216
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
agtagcatta acatccaatc agctacgcaa tacaaaactc cgaacacctg cttctgactg    60
ggtgctg                                                              67

<210> SEQ ID NO 217
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
cagcacccag tcagaagcag gtgttcggag ttttgtattg cgtagctgaa tgctgtagct    60
caacatg                                                              67

<210> SEQ ID NO 218
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
ccatgatgct attgacatca gcatttacaa caggctaatt aag                      43

<210> SEQ ID NO 219
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
acgtcagcac tattagtaga atttgcatat ccgcaa                              36

<210> SEQ ID NO 220
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220

```
gaactggagt agcac                                                      15
```

<210> SEQ ID NO 221
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221

```
gaactggagt agcac                                                      15
```

<210> SEQ ID NO 222
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222

```
gaactggagt agcac                                                      15
```

<210> SEQ ID NO 223
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223

```
gaactggagt agcac                                                      15
```

<210> SEQ ID NO 224
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224

```
ttcaattaat atcaaaaaac tatat                                           25
```

<210> SEQ ID NO 225
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225

```
tttagtatca tatgcgctca ac                                              22
```

<210> SEQ ID NO 226
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226

```
tctaaagtac ggtgtataag agagtcagat cat                                  33
```

```
<210> SEQ ID NO 227
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
gtgtaggtta agcaataaag caaaaggtgg catcat                              36

<210> SEQ ID NO 228
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
gtgctactcc agttc                                                    15

<210> SEQ ID NO 229
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
ccaacgttat acaaattctt atttactcag ggcactgcaa gcaattgtgg tcccaatggg   60
ctgagta                                                             67

<210> SEQ ID NO 230
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
tactcagccc attgggacca caattgcttg cagtgccctg agtattaatg ctgtagctca   60
acatg                                                               65

<210> SEQ ID NO 231
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
tactcagccc attgggacca caattgcttg cagtgccttt tttttaatg ctgtagctca    60 acatg                                                               65

<210> SEQ ID NO 232
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 232
tactcagccc attgggacca caattgcttg tttttttttt tttttaatg ctgtagctca     60 acatg                                                                65

<210> SEQ ID NO 233
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
tactcagccc attgggacca caattttttt tttttttttt tttttaatg ctgtagctca     60 acatg                                                                65

<210> SEQ ID NO 234
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
tactcagccc attgggtttt tttttttttt tttttttttt tttttaatg ctgtagctca     60 acatg                                                                65
```

DNA ORIGAMI DEVICES

CROSS-REFERENCE TO RELATED APPLICATIONS

This Application is a 35 U.S.C. §371 National Phase Entry Application of International Application No. PCT/US2011/059352 filed Nov. 4, 2011, which designates the U.S., and which claims the benefit under 35 U.S.C. §119(e) of U.S. Provisional Patent Application No. 61/410,102, filed Nov. 4, 2010, which is hereby incorporated herein by reference, including the computer program listing appended to its disclosure. The computer program listing includes the file programlisting.txt which includes a listing for robot.json.

SEQUENCE LISTING

The instant application contains a Sequence Listing which has been submitted in ASCII format via EFS-Web and is hereby incorporated by reference in its entirety. Said ASCII copy, created on Apr. 30, 2013, is named 002806-073572-US SequenceListing and is 67,040 bytes in size.

BACKGROUND

One of the long-standing challenges in medicine is the targeted delivery of therapeutic molecules to appropriate cells. For example, drugs that have a beneficial therapeutic effect if delivered to the proper cell population will often cause severe side-effects if delivered elsewhere. Unfortunately, the specific targeting of a particular cell type is often not possible with existing drug delivery technologies. Thus, there exists a great need for novel compositions and methods useful in the selective delivery of therapeutic agents.

BRIEF DESCRIPTION OF THE DRAWINGS

FIG. 2 shows the scaffold sequence of an exemplary DNA origami device.

FIG. 3 shows the sequences of the staple strands of an exemplary DNA origami device.

FIGS. 4A-4G show the effects of exemplary aptamer-encoded latch schemes on the interactions between a DNA origami device and cell populations.

FIGS. 5A-5F show the selective targeting and manipulation of cells by exemplary DNA origami devices.

DETAILED DESCRIPTION

Figure 1A:
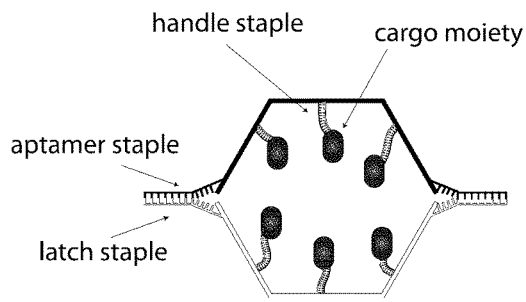
FIGS. 1A-1G show schematic and transmission electron microscopy images of an exemplary DNA origami device.

Provided herein are DNA origami devices useful in, for example, the targeted delivery of therapeutic agents particular cell populations. Such devices are able to sequester potentially biologically active moieties within the interior of the device, thereby sterically preventing them from interacting with inappropriate cell populations.

In some embodiments, the DNA origami device is held in a closed configuration by a molecular latch that is capable of interacting with an antigen. When the molecular latch is contacted by the antigen, the DNA origami device transitions to an open configuration. When the DNA origami device is in an open configuration, the previously sequestered biologically active moieties are able to interact with cells proximal to the DNA origami device. Thus, by designing the molecular latch to interact with a particular antigen, the DNA origami device can be targeted to deliver biologically active moieties to certain cell populations that express the antigen, while preventing the moieties from interacting with other cell populations.

In some embodiments, the DNA origami device may be introduced into a subject to act as a scavenger. In such embodiments, the DNA origami device is able to bind to and sequester specific moieties that it encounters in the subject. Applications include, for example, detecting antigens or antibodies for diagnostic purposes, sequestering undesired moieties for clearance, and artificial antigen-presenting cells, among others.

DNA Origami

DNA origami structures incorporate DNA as a building material to make nanoscale shapes. In general, the DNA origami process involves the folding of one or more long, "scaffold" DNA strands into a particular shape using a plurality of rationally designed "staple" DNA strands. The sequences of the staple strands are designed such that they hybridize to particular portions of the scaffold strands and, in doing so, force the scaffold strands into a particular shape. Methods useful in the making of DNA origami structures can be found, for example, in Rothemund, P. W., *Nature* 440:297-302 (2006); Douglas et al., *Nature* 459:414-418 (2009); Dietz et al., *Science* 325:725-730 (2009); and U.S. Pat. App. Pub. Nos. 2007/0117109, 2008/0287668, 2010/0069621 and 2010/0216978, each of which is incorporated by reference in its entirety. Staple design can be facilitated using, for example, CADnano software, available at http://www.cadnano.org.

Thus, in some embodiments, the DNA origami device (or "robot" or "DNA robot" or "DNA nanorobot") may include a scaffold strand and a plurality of rationally designed staple strands. The scaffold strand can have any sufficiently non-repetitive sequence. For example, in certain embodiments, the scaffold strand has an M13-derived sequence, such as the M13mp18-derived sequence provided in FIG. 2.

The sequences of the staple strands are selected such that the DNA origami device has at least one shape in which biologically active moieties can be sequestered. In some embodiments, the DNA origami can be of any shape that has at least one inner surface and at least one outer surface. In general, an inner surface is any surface area of the DNA origami device that is sterically precluded from interacting with the surface of a cell, while an outer surface is any surface area of the DNA origami device that is not sterically precluded from interacting with the surface of a cell. In some embodiments, the DNA origami device has one or more openings (e.g., two openings), such that an inner surface of the DNA origami device can be accessed by sub-cellular sized particles. For example, in certain embodiments the DNA origami device has one or more openings that allow particles smaller than 10 µm, 5 µm, 1 µm, 500 nm, 400 nm, 300 nm, 250 nm, 200 nm, 150 nm, 100 nm, 75 nm, 50 nm, 45 nm or 40 nm to contact an inner surface of the DNA origami device.

In certain embodiments, the DNA origami device is able to change shape (conformation) in response to one or more certain environmental stimuli. Thus, in some embodiments, an area of the DNA origami device may be an inner surface of the device when the device takes on some conformations, but may be an outer surface of the device when the device takes on other conformations. In some embodiments, the DNA origami device can respond to certain environmental stimulus by taking on a conformation in which it has little or no inner surface.

In some embodiments, the staple strands of the DNA origami device are selected such that the DNA origami device is substantially barrel- or tube-shaped. In such embodiments, the inner surface of the DNA origami device is the surface on the inside of the barrel, while the outer surface of the DNA origami device is the outside of the barrel. In such embodiments, the staples of the DNA origami device can be selected such that the barrel shape is closed at both ends or is open at one or both ends, thereby permitting sub-cellular sized particles to enter the interior of the barrel and access its inner surface. In certain embodiments, the barrel shape of the DNA origami device is a substantially hexagonal tube.

In some embodiments, the staple strands of the DNA origami device are selected such that the DNA origami device has a first domain and a second domain, wherein the first end of the first domain is attached to the first end of the second domain by one or more single-stranded DNA hinges, and the second end of the first domain is attached to the second domain of the second domain by the one or more molecular latches, as described below. In certain embodiments, the plurality of staples are selected such that the second end of the first domain becomes unattached to the second end of the second domain if all of the molecular latches are contacted by their respective external stimuli, as described herein.

Handle Domains

In certain embodiments, the DNA origami device includes elements bound to a surface of its DNA origami structure (e.g. molecular latches, handles, tethered moieties, etc.). Such elements can be precisely positioned on the DNA origami device through the use of extended staple strands that include a domain having a sequence that does not hybridize to the scaffold strand. The additional elements can be directly or indirectly attached to such staples. As used herein, the term "directly bound" refers to a nucleic acid that is covalently bonded an entity. In contrast, the term "indirectly bound" refers to a nucleic acid that is attached to an entity through one or more non-covalent interactions.

In some embodiments, the DNA origami device includes a staple having extensions capable of binding to a moiety (termed a "handle" domain). In such embodiments, such staples can be synthesized to have at least two domains, a staple domain and a handle domain. The staple domain is a sequence of the staple that hybridizes to the scaffold strand to contribute to the formation and stability of the DNA origami structure. The handle domain contains additional nucleic acid sequence that is not necessary for the creation of the DNA origami structure.

In some embodiments, the handle domain can be directly bound to a moiety. For example, the staple can be synthesized with a particular moiety attached, or covalently bonded to a moiety prior to or following its incorporation into the DNA origami structure.

In some embodiments, the handle domain can be indirectly bound to a moiety. For example, before, during or after the formation of the DNA origami structure, the handle sequences can available to be hybridized by oligonucleotides having a complementary DNA sequence. Thus, such staples can be indirectly bound by hybridizing the handle domain to another nucleic acid that has a nucleic acid sequence complementary to the handle and that is itself either directly or indirectly bound to a particular moiety.

The staples of a DNA origami device can be selected such that a handle domain is positioned on any surface of the device, including inner surfaces and outer surfaces. In certain embodiments, the staples are selected such that a handle domain is positioned on an inner surface of the DNA origami device. Handle positioned on an inner surface of the DNA origami device and moieties bound by such handles are sequestered, and therefore sterically precluded from interacting with the surface of cells. Inner surface positioned handles are useful, for example, for preventing bound biologically active moieties from interacting with inappropriate cell populations and thereby inducing potentially harmful effects.

In certain embodiments, the staples are selected such that a handle domain is positioned on an outer surface of the DNA origami device. Such handles can be bound by, for example, molecular entities useful for delivery, detection or recapture of the DNA origami device. In some embodiments, for example, such outer handles can be bound by polyethylene glycol (PEG), carrier proteins, or other moieties capable of protecting the DNA origami device from a physiological environment. In certain embodiments, such outer handles can be bound by a detectable moiety, such as a fluorophore or a quantum dot. In certain embodiments, such outer handles can themselves facilitate the recapture of the DNA origami device, or can be bound by moieties that facilitate the device's recapture, such as antibodies, epitope tags, biotin or streptavidin.

As discussed herein, in certain embodiments the DNA origami device is able to undergo a transition from a first conformation to a second conformation in response to an environmental stimulus. In certain embodiments, a handle that was positioned on an inner surface of the DNA origami device prior to the conformational change may become located on an outer surface of the DNA origami device after the conformational change. In some embodiments, a handle that was positioned on an outer surface of the DNA origami device prior to the conformational change may become located on an inner surface of the device following the conformational change. An "open configuration" is one in which a moiety of interest (or its handle) is located on an outer surface. A "closed configuration" is one in which a moiety of interest (or its handle) is located on an inner surface. Thus, a device when adopting a particular conformation may simultaneously have an open configuration as to one moiety and a closed configuration as to another.

Molecular Latches

In some embodiments, the staples of the DNA origami devices are selected such that the DNA origami device is held in a particular conformation by a molecular latch. In general, such latches are formed from two or more staple stands, including at least one staple strand having at least one stimulus-binding domain that is able to bind to an external stimulus, such as a nucleic acid, a lipid or a protein, and at least one other staple strand having at least one latch domain that binds to the stimulus binding domain. The binding of the stimulus-binding domain to the latch domain supports the stability of a first conformation of the DNA origami device. The contacting of one or more of the stimulus-binding domains by an external stimulus to which it can bind displaces the latch domain from the stimulus-binding domain. This disruption of the molecular latch weakens the stability of the first conformation and may cause the DNA origami device to transition to a second conformation. In certain embodiments, this conformational change may result in previously sequestered moieties becoming externally presented and thereby rendering them capable of exerting a biological effect upon proximal cells.

In certain embodiments, the staple strands of a DNA origami device are selected such that the DNA origami device includes multiple molecular latches. For example, in certain embodiments, the DNA origami device includes two molecular latches. In some embodiments the various molecular latches may recognize different external stimuli, while in certain embodiments they recognize the same external stimuli. In certain embodiments, multiple external-stimuli binding domains and/or latch domains may be present on a single staple strand. In some embodiments, a stimuli-binding domain or a latch domain may span multiple staple strands which come together when the stimulus binds. In some embodiments, a stimuli-binding domain may bind multiple latch domains, or multiple stimuli-binding domains may bind a single latch domain.

The external stimulus to which the stimulus-binding domain can be any type of molecule including, but not limited to, a protein, a nucleic acid, a lipid, a carbohydrate and a small molecule. In certain embodiments, the external stimulus is preferentially expressed by a particular population of cells to be targeted by the DNA origami device. In such embodiments, the external stimulus may be present on or near the surface of the targeted cell population. For example, in certain embodiments the external stimulus is a cancer cell-specific antigen. In some embodiments the external stimulus is a molecule that is able to specifically bind to a particular population of cells. For example, the external stimulus can be a moiety bound to an antibody specific for an antigen expressed by a particular population of cells (e.g. a cancer cell-specific antigen).

The stimulus-binding domain is capable of forming a bond with a latch domain that is displaced upon the binding of an external stimulus. In certain embodiments, the stimulus binding domain binds to the external stimulus with a higher affinity than it binds to the latch domain.

In certain embodiments, the stimulus-binding domain is an aptamer domain. Aptamer domains have one or more aptamer sequences that are capable of binding to a particular antigen (e.g., a particular protein, a peptide, a lipid, a carbohydrate or a small molecule). Aptamers can be designed to target essentially any antigen of interest using methods known in the art. For example, methods of designing aptamers specific for a target of interest can be found in U.S. Pat. Nos. 5,582,981, 5,756,291, 5,840,867, 7,745,607 and Tang et al., *Anal. Chem.* 79:4900-4907 (2007), each of which are incorporated by reference in their entirety.

In embodiments where the stimulus-binding domain is an aptamer domain, the latch domain to which it binds will have a nucleotide sequence able to hybridize to at least a portion of the aptamer domain. In certain embodiments, the latch domain may include a sequence that is perfectly complementary to the aptamer domain or a portion of the aptamer domain (i.e. that is able to base pair at every nucleotide with at least a portion of the aptamer domain sequence). In some embodiments, however, the sequence of the latch domain is less than perfectly complementary to the aptamer domain sequence but is still able to hybridize to an aptamer domain sequence acid under certain conditions. Thus, in certain embodiments the sequence of the latch domain is at least 10%, 20%, 30%, 40%, 50%, 60%, 65%, 70%, 75%, 80%, 85%, 90% or 95% complementary to a sequence of the aptamer domain. In some embodiments, the sequence of the latch domain is selected such that the aptamer domain binds to it with a lower affinity than the aptamer domain binds to its antigen.

In certain embodiments, the external stimulus is a nucleic acid. In such embodiments, the stimulus-binding domain can have a nucleic acid sequence that is able to hybridize to at least a portion of the external stimulus. In certain embodiments, the stimulus-binding domain may include a sequence that is perfectly complementary to the sequence of the external stimulus or a portion of the sequence of the external stimulus. In some embodiments, however, the sequence of the stimulus-binding domain is less than perfectly complementary to the sequence of the external stimulus, but is still able to hybridize to a sequence of the external stimulus under certain conditions. Thus, in certain embodiments the sequence of the stimulus-binding domain is at least 10%, 20%, 30%, 40%, 50%, 60%, 65%, 70%, 75%, 80%, 85%, 90% or 95% complementary to a sequence of the external stimulus.

In embodiments where the stimulus-binding domain binds to a nucleic acid stimulus, the latch domain to which it binds will have a nucleotide sequence able to hybridize to at least a portion of the stimulus-binding domain. In certain embodiments, the latch domain may include a sequence that is perfectly complementary to the sequence of the stimulus-binding domain or a portion of the sequence of the stimulus-binding domain. In some embodiments, however, the sequence of the latch domain is less than perfectly complementary to the stimulus-binding domain sequence but is still able to hybridize to a stimulus-binding domain sequence acid under certain conditions. Thus, in certain embodiments the sequence of the latch domain is at least 10%, 20%, 30%, 40%, 50%, 60%, 65%, 70%, 75%, 80%, 85%, 90% or 95% complementary to a sequence of the stimulus-binding domain. In some embodiments, the sequence of the latch domain is selected such that the stimulus-binding domain binds to it with a lower affinity than the stimulus-binding domain binds to the external stimulus. In certain embodiments, the latch domain is designed such that its sequence is not perfectly complementary to the sequence of the stimulus-binding domain in order to improve the sensitivity of the molecular latch. In certain embodiments, the latch domain contains at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 nucleotides that are not complementary to the sequence of the stimulus-binding domain. The latch domain may contain more than 33 nucleotides that are not complementary to the sequences of the stimulus-binding domain. In some embodiments, the stimulus-binding domain further comprises a single-stranded toehold when bound to the latch domain.

In some embodiments, the stimulus-binding domain comprises a non-nucleic acid moiety that is able to bind to an external stimulus. For example, in certain embodiments the stimulus-binding domain comprises an antibody, an antibody fragment, a protein or a peptide that is able to bind to an antigen or ligand present on or near the surface of a targeted cell. In such embodiments, the latch domain would comprise a moiety (such as an antibody, an antibody fragment, a protein or a peptide) that is also able to bind to the stimulus-binding domain. As with the aptamer domains, the binding of the stimulus to the stimulus-binding domain causes the displacement of the latch domain from the stimulus-binding domain. This displacement can either be a direct displacement (e.g., the stimulus and the latch domain bind the same epitope of the stimulus-binding domain), or can be indirect displacement (e.g. the binding of the stimulus to the stimulus-binding domain causes a conformational change in the stimulus-binding domain such that the latch domain is no longer able to bind).

In some embodiments, the DNA origami device may further include a "locking" or "support" staple having a single-stranded toehold domain. The locking staple is selected such that the presence of the locking staple on the DNA origami device prevents its transition from a first conformation to a second conformation (e.g. from a closed configuration to an open configuration). Such a locking staple may, for example, improve the proper self-assembly of the DNA origami device in the first conformation. In some embodiments, the DNA origami device may include a plurality of locking staples. For example, in some embodiments the DNA origami device will include 2, 3, 4, 5, 6, 7, 8 or more locking staples. Contacting a locking staple with an oligonucleotide having a complementary sequence displaces the locking staple for the DNA origami device, thereby "unlocking" the device and permitting it to transition to the second conformation if provided with the appropriate external stimulus. In certain embodiments, the single-stranded toehold domain of the locking staple extends from the inner surface of the DNA origami device. In some embodiments, the single-stranded toehold domain of the locking staple extends from the outer surface of the DNA origami device.

In some embodiments, the staples of the DNA origami device are selected such that the device emits one or more different detectable signals depending upon its conformation. For example, the DNA origami device may include at least one staple bound to a fluorophore (a "signal staple") and at least one staple bound to a quencher (a "quencher staple"). The binding of staples to fluorophores or quenchers can be either direct or indirect. The staple strands of the DNA origami device can be selected such that the transition from one conformation (e.g., an open configuration) to a second conformation (e.g., a closed configuration) changes the distance between at least one fluorophore and at least one quencher, thereby changing a signal output of the device.

Bound Moieties

In certain embodiments, staple strands of the DNA origami device are selected such that one or more handle domains are positioned on the inner surface of the DNA origami device. In certain embodiments, at least some of those handle domains are bound by a moiety. Such a moiety can be attached to the handle domain using any method known in the art. For example, the moiety can be covalently bonded to handle domain. The moiety can also be indirectly attached to the handle domain by, for example, hybridizing to the handle domain of a staple strand, as described above.

In certain embodiments, the DNA origami device includes a plurality of internally positioned handle domains. In such embodiments, the handle domains can all bind to a single type of moiety, or can bind to a plurality of distinct moieties. In some embodiments, the handle domains bind to a plurality of distinct moieties in a predefined a stoichiometric ratio. In certain embodiments, the moieties are bound to handles of the DNA origami device at predetermined positions. Such stoichiometric and spatial control of moiety binding is useful in, for example, the synergistic delivery of multiple biologically active moieties for combinational drug therapy.

Any type of moiety can be bound to the handle domains of the DNA origami device. For example, in certain embodiments the moiety includes at least one of: an antibody, an antibody fragment, a cell surface receptor ligand, a biologically active fragment of a cell surface receptor ligand, a small molecule, a nucleic acid, a DNAzyme, an aptamer, a lipid, a glycan, a glycoprotein, a glycolipid, a proteoglycan, a nanoparticle, a quantum dot, a fluorophore, and a nanocrystal. In some embodiments the moiety includes a fusion of one or more of the above moiety types.

In certain embodiments, the moiety bound to the handle of the DNA origami device may include an antibody. As used herein, the term "antibody" includes full-length antibodies and any antigen binding fragment (i.e., "antigen-binding portion") or single chain thereof. The term "antibody" includes, but is not limited to, a glycoprotein comprising at least two heavy (H) chains and two light (L) chains inter-connected by disulfide bonds, or an antigen binding portion thereof. Antibodies may be polyclonal or monoclonal; xenogeneic, allogeneic, or syngeneic; or modified forms thereof (e.g., humanized, chimeric).

As used herein, the phrase "antigen-binding portion" of an antibody, refers to one or more fragments of an antibody that retain the ability to specifically bind to an antigen. The antigen-binding function of an antibody can be performed by fragments of a full-length antibody. Examples of binding fragments encompassed within the term "antigen-binding portion" of an antibody include (i) a Fab fragment, a monovalent fragment consisting of the $V_H$, $V_L$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_H$ and $V_L$ domains of a single arm of an antibody, (v) a dAb fragment (Ward et al., (1989) Nature 341:544 546), which consists of a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_H$ and $V_L$, are coded for by separate genes, they can be joined, using recombinant methods, by a synthetic linker that enables them to be made as a single protein chain in which the $V_H$ and $V_L$ regions pair to form monovalent molecules (known as single chain Fv (scFv); see e.g., Bird et al. (1988) Science 242:423 426; and Huston et al. (1988) Proc. Natl. Acad. Sci. USA 85:5879 5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

The present DNA origami devices permit use of thermally labile moieties as payload, provided that the origami structure assembled in the closed orientation includes an opening large enough for the moiety to enter the device and become bound. Assembly normally requires a temperature high enough to denature DNA; denaturation can start at temperatures as low as 60° C. and is typically carried out at a temperature in the range of 60-95° C., frequently at 95° C. Many potentially useful moieties cannot retain biological activity following exposure to such temperatures. But because the device may be fully assembled (i.e., by a thermal annealing process) in the closed orientation yet leave the handle domains accessible to the moiety, the moiety need not be included in the annealing mixture; it can instead be added later, once the reaction has cooled.

Methods of Use

A method of delivering one or more moieties to a cell having an external stimulus (e.g. an antigen) on or near its surface may include contacting the cell with a latched DNA origami device that is carrying the moiety, thereby allowing the external stimulus to displace a latch domain from an stimulus-binding domain, and allowing the moiety to contact the cell.

As described above, in certain embodiments, contacting a DNA origami device with an external stimulus present on the surface of a cell causes the DNA origami device to transition from a closed configuration to an open configuration. In such embodiments, this conformational change will cause previously internal handle domains to become external handle domains, thereby allowing their bound moieties to interact with the cell. In certain embodiments, the moieties remain bound to the handle domains after the transition to an open configuration. Thus, in certain embodiments a method of treating a disease or disorder in a subject may include administering to the subject a DNA origami device as disclosed herein that delivers an effective amount of a therapeutic moiety to one or more targeted cell in the subject. Multi-drug therapy may be delivered by these methods by attaching different drug moieties to various handles. The relative amounts of moieties may be precisely controlled in this manner, because each handle can be made receptive to specific moieties. So, for example, if three moieties A, B, and C are to be delivered in a stoichiometric ratio of 2:1:3, a DNA origami device can be made with staple strands having domains such that there are two handles specific for moiety A, and three handles specific for moiety C, for every handle that is specific for moiety B.

A wide variety of diseases and disorders are susceptible to treatment by these methods. Diseases or disorders characterized by the absence of a tangible mass that can be physically targeted may be especially well-suited to the present methods of treatment. Examples include blood-borne illnesses, such as a blood-borne cancer (e.g. a leukemia) or an autoimmune disease.

In some embodiments, the transition to the open configuration or the interaction with the cell causes the moiety to be released by the handle domain. For example, the handle domain can include an aptamer sequence specific for an antigen present on the surface of the cell. In such embodiments, the binding of the antigen to the handle domain displaces the moiety from the handle domain. Thus, in these embodiments, the DNA origami device not only delivers the therapeutic moiety to a cell, it can achieve a high local concentration of the therapeutic moiety around intended targets while sparing unintended targets from undesirable side-effects. The released therapeutic moiety will also be freer to interact with the cell, possibly being internalized for therapeutic effect.

In certain embodiments, a method of sequestering a particle smaller than the inner cross-section of the DNA origami device in size may include contacting the particle with a DNA origami device that includes an internally-bound moiety capable of specifically binding to the particle and wherein the structure of the DNA origami device has one or more openings that allow the particle to contact the internally bound moiety. Such methods are useful, for example, for sequestering potentially harmful molecules in a subject, thereby reducing the amount such molecules interact with cells. It is not necessary that such scavenger DNA origami devices have the ability to undergo a conformational change to an open state. A scavenging device may be used without a moiety pre-loaded; in this case, the handles may include aptamer domains or chemical modifications that bind particles of interest. Alternatively (or in addition), a scavenging device may be preloaded with a moiety that itself binds a particle of interest.

In certain embodiments, the DNA origami device can then deliver scavenged particles to targeted cells. For example, in some embodiments, scavenged particles are sequestered, as described above, in DNA origami devices. The devices then encounter a target cell bearing the appropriate stimulus to open the latch(es), thereby causing the device to open and deliver the scavenged particle to the target cell. In this way, the DNA origami device can act, for example, as an artificial antigen presenting cell, presenting scavenged, moiety-bound antigens to T cells or B cells in conjunction with additional biologically active moieties. By selecting the amount of antigen presented and the nature of the additional biologically active moieties, such DNA origami devices can, for example, induce the targeted immune cell to undergo apoptosis, to become activated, to become tolerized, or to differentiate into a particular sub-type of immune cell. Such DNA origami devices are useful, for example, in the induction of an immune response against a cancer or pathogenic agent (e.g. a virus or bacterium), or in the inhibition of an allergic or autoimmune response.

In certain embodiments, a method of detecting a particle smaller than the inner cross-section of the DNA origami device in size may include contacting the particle with a DNA origami device that includes an internally-bound moiety capable of specifically binding to the particle and wherein the structure of the DNA origami device has one or more openings that allow the particle to contact the internally bound moiety. In such embodiments, a DNA origami device previously introduced into a subject may be retrieved from a subject and the presence of sequestered particles detected using methods known in the art. For example, the DNA origami device can be induced to transition into an open state by contacting it with an external stimulus that displaces a latch domain from a stimulus-detecting domain and the particle detected using a probe (e.g., an antibody or antibody fragment). In some embodiments, the presence of the particle in the DNA origami device is detected while the particle remains sequestered. In some embodiments, the DNA origami device is bound to a solid support prior to or during the detection of the particle. In certain embodiments, the solid support includes an external stimulus capable of displacing a latch domain from a stimulus-detecting domain, thereby opening the DNA origami device on the support.

EXAMPLES

Example 1

Design and Synthesis of a DNA Origami Device

Described herein is the design and synthesis of a DNA origami device capable of selectively interfacing with cells to manipulate their biology. A DNA origami device in the form of a hexagonal pod with dimensions of approximately 35×35×45 nm$^3$ in size was designed using CADnano, a computer-aided design tool for DNA origami. FIG. 1A is a schematic front view of an exemplary DNA origami device loaded with proteins. The pod is made of a single 7308-base M13mp18-derived scaffold strand hybridized to a plurality of rationally-designed staple strands. The pod structure includes two domains that are covalently attached in the rear by single-stranded DNA hinges and can be non-covalently fastened in the front by DNA-aptamer-based latches. Design blueprints are provided in the computer program listing submitted with U.S. provisional application Ser. No. 61/410, 102, which provides the "robot.json" file containing the structure of the illustrated device for use with CADnano. The sequence of the M13mp18-derived scaffold strand is provided in FIG. 2. The sequences of the staple strands are provided in FIG. 3. (Abbreviations within the sequences indicating chemical modifications follow the nomenclature used by Integrated DNA Technologies, Inc.: /5BioTEG/ indicates 5' Biotin-TEG (tetra-ethyleneglycol); /5AmMC6/ indicates 5' Amino Modifier C6 (6-(4-Monomethoxytritylamino)hexyl-(2-cyanoethyl)-(N,N-diisopropyl)-phosphoramidite); /5ThioMC6-D/ indicates 5' Thiol Modifier C6 S—S (1-O-Dimethoxytrityl-hexyl-disulfide,1'-[(2-cyanoethyl)-(N,N-diisopropyl)]-phosphoramidite); /5DTPA/ indicates 5' Dithiol; /36-FAM/ indicates 3' 6-FAM™ (6-carboxyfluorescein); /5IAbFQ/ indicates 5' Iowa Black® FQ; /5TYE665/ indicates 5' TYE™ 665; and /3IAbRQSp/ indicates 3' Iowa Black® RQ-Sp.) Staples 179-190 include handle domains. The handle domain sequence is GTGCTACTCCAGTTC (SEQ ID NO: 228), and it is separated from the staple domain by a 2-base TT spacer. Staples 219-222 are typical linker strands, which are chemically attached to a moiety. The linker strands include an anti-handle domain, GAACTGGAGTAGCAC (SEQ ID NO: 220), which is complementary to the handle domain. In this example, all the handle domains are the same; in practice, distinct handle domains can be used in order to load more than one type of moiety.

To modify the device such that it emits a detectable signal upon opening, staples 175-178 can be replaced by staples 223-226. If such a substitution is made, staples 223 and 226 bind to the top domain of the device, while staples 224 and 225 bind to the bottom domain of the device (as the device is illustrated in FIG. 1A). As indicated in FIG. 3, staples 223 and 225 are modified with fluorophores, while staples 224 and 226 are modified with quenchers. The staples are positioned such that, when the device is closed the 3' end of staple 223 is less than 2 nm away from the 5' end of staple 224, while the 3' end of staple 225 is less than 2 nm away from the 5' end of staple 226. At this distance, the fluorescent signals produced by the fluorophores bound to staples 223 and 225 are quenched by the quenchers bound to staples 224 and 226. When the device is in an open configuration, the fluorophores bound to staples 223 and 225 move apart from the quenchers bound to staples 224 and 226, respectively, increasing the signal output of the device.

Figure 1B:
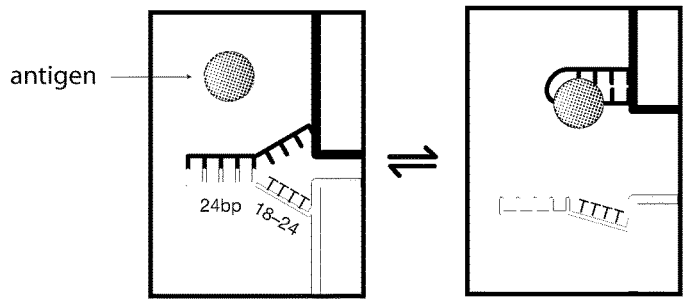
Figure 1D:
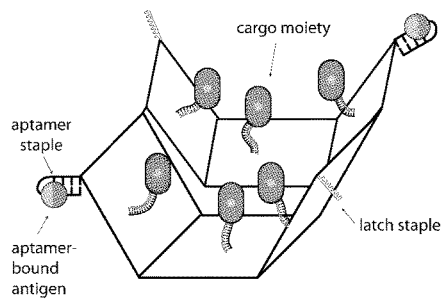
Figure 1E:
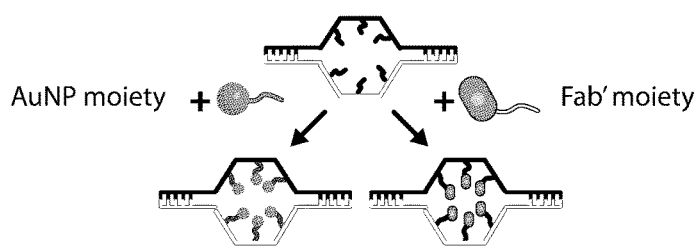
Figure 1C:
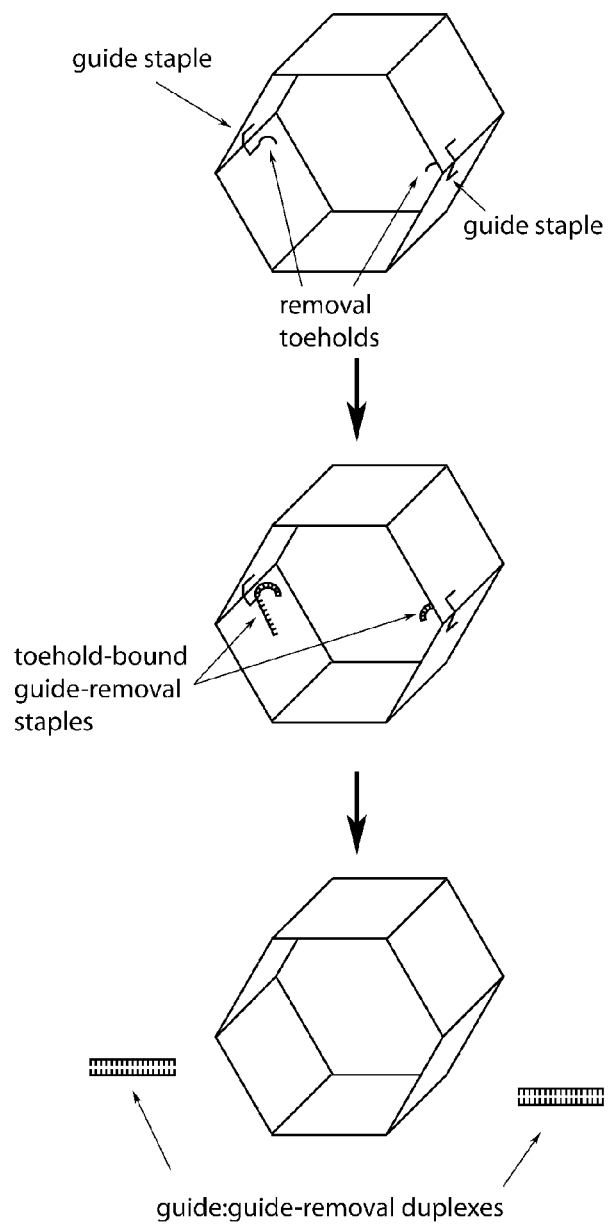

Initial self-assembly of the DNA origami device was performed using in a one-pot reaction, in which 196 oligonucleotide staple strands directed the scaffold strand into its target shape during a thermal-annealing ramp of rapid heating followed by slow cooling. Two support staples that span the top and bottom domains were incorporated adjacent to the latch sites, and were found to increase the folding yield to 97.5% of the devices in the closed state, as compared to 48% closed when folded without support staples. The support staples included 8-base toehold overhangs and were removed after folding and purification through the addition of fully complementary strands to the mixture (FIG. 1C).

In order to operate the device in response to a wide array of input types, including proteins, a DNA-aptamer-based latch mechanism was designed that opens in response to binding antigen keys. FIG. 1B is a schematic diagram of an exemplary aptamer latch mechanism that includes a DNA aptamer domain and its complementary latch domain. In the presence of its cognate antigen, the two strands dissociate. A DNA duplex having an aptamer strand and its complementary latch strand were designed such that the two strands can be separated via intramolecular displacement by the aptamer strand's cognate antigen. Aptamer-complement duplexes were incorporated on the left and right sides of the front of the device, such that the aptamer strands are attached to the top domain and the complement strands are attached to the bottom domain (FIG. 1A). Similar to a combination lock, the pod is able to open only upon disassembly of both latches, driven by each aptamer recognizing its own cognate target. FIG. 1D depicts an exemplary DNA origami device in its open configuration. In such a configuration, the two halves of the device remain connected by scaffold hinges in the rear. A number of different aptamer sequences were used to make DNA origami devices, including aptamers previously described as binding to platelet-derived growth factor (PDGF), Ramos and CCRF-CEM cell-surface antigens.

The exemplary DNA origami device had twelve staple strands positioned inside of its DNA origami structure that had single-stranded 3' extensions capable of serving as "handles" for the loading of molecular payloads. The attachment points were arranged in an inward-facing ring inside the pod (FIG. 1A). These handles were able to be loaded molecular payloads covalently attached to the 5' end of a 15-base single-stranded DNA oligonucleotide linkers having sequence complementarity to the oligonucleotide handles (FIG. 1E). Two types of cargo were loaded into the robot: 5-nm gold nanoparticles (Sigma) covalently attached to 5'-thiol-modified linkers, and various Fab' antibody fragments that were covalently attached to 5'-amine modified linkers.

Figure 1F:
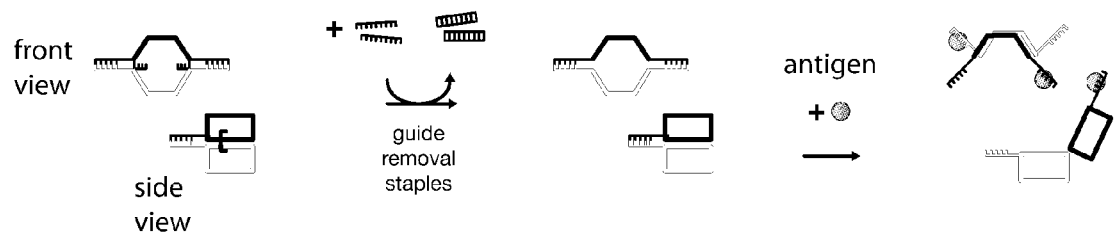

FIG. 1F is a schematic illustration depicting the function of an exemplary DNA origami device. Following initial self-assembly, the DNA origami device is "unlocked" by treating the device with nucleic acid strands that are complementary to the device's support staples, which causes the support staples to disassociate from the device. Binding of the device's aptamer strands to its cognate antigen causes the device to undergo a conformational change and expose its molecular payload.

Figure 1G:
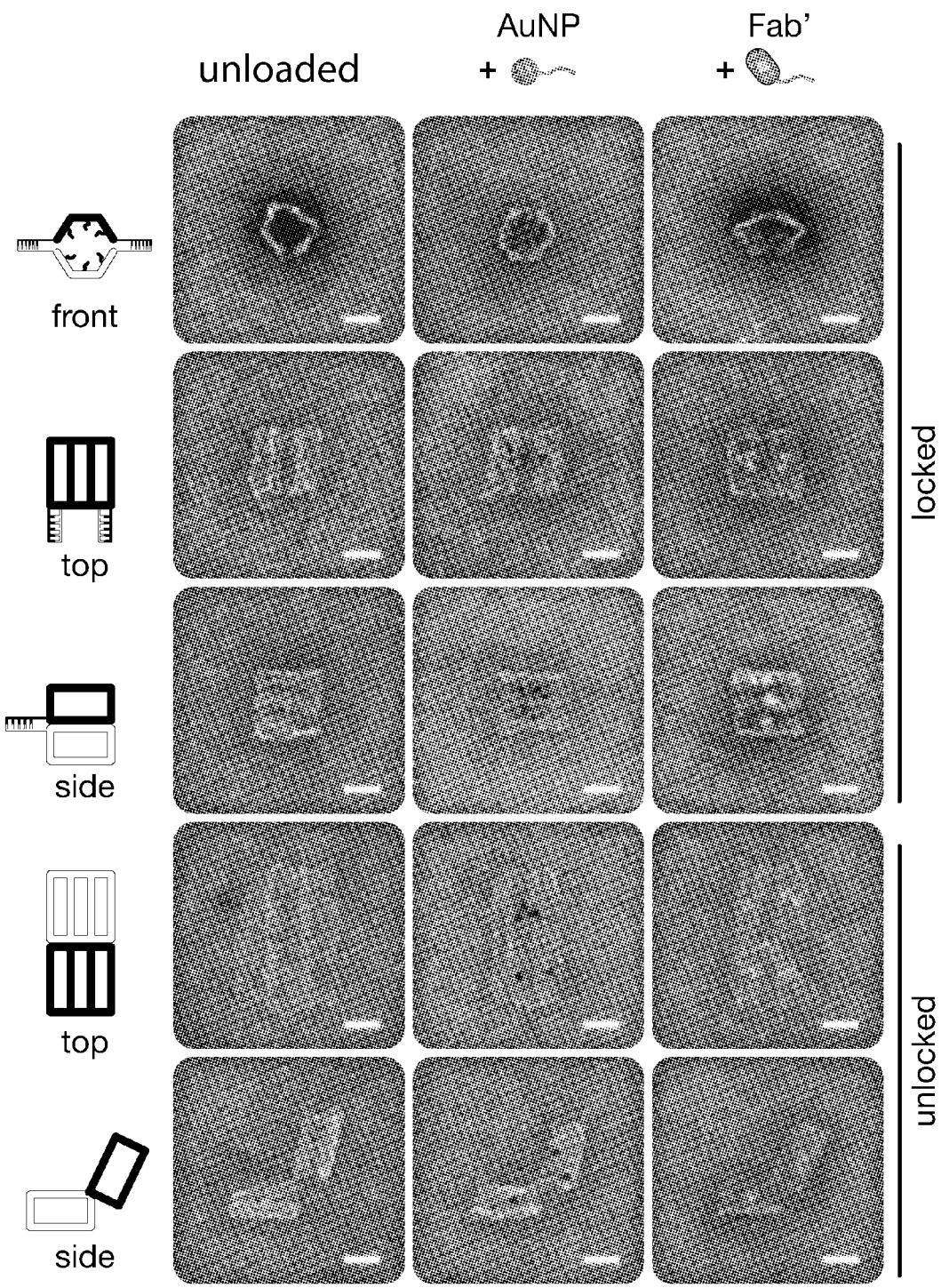

Negative-stain transmission electron microscopy (TEM) was used to analyze exemplary devices (FIG. 1G). The left column of micrographs depicts unloaded devices, the center column depicts devices loaded with 5 nm gold-nanoparticles and the right column depicts devices loaded with Fab' fragments.

Example 2

Use of a DNA Origami Device for Target-Specific Signal Delivery

Figure 4A:
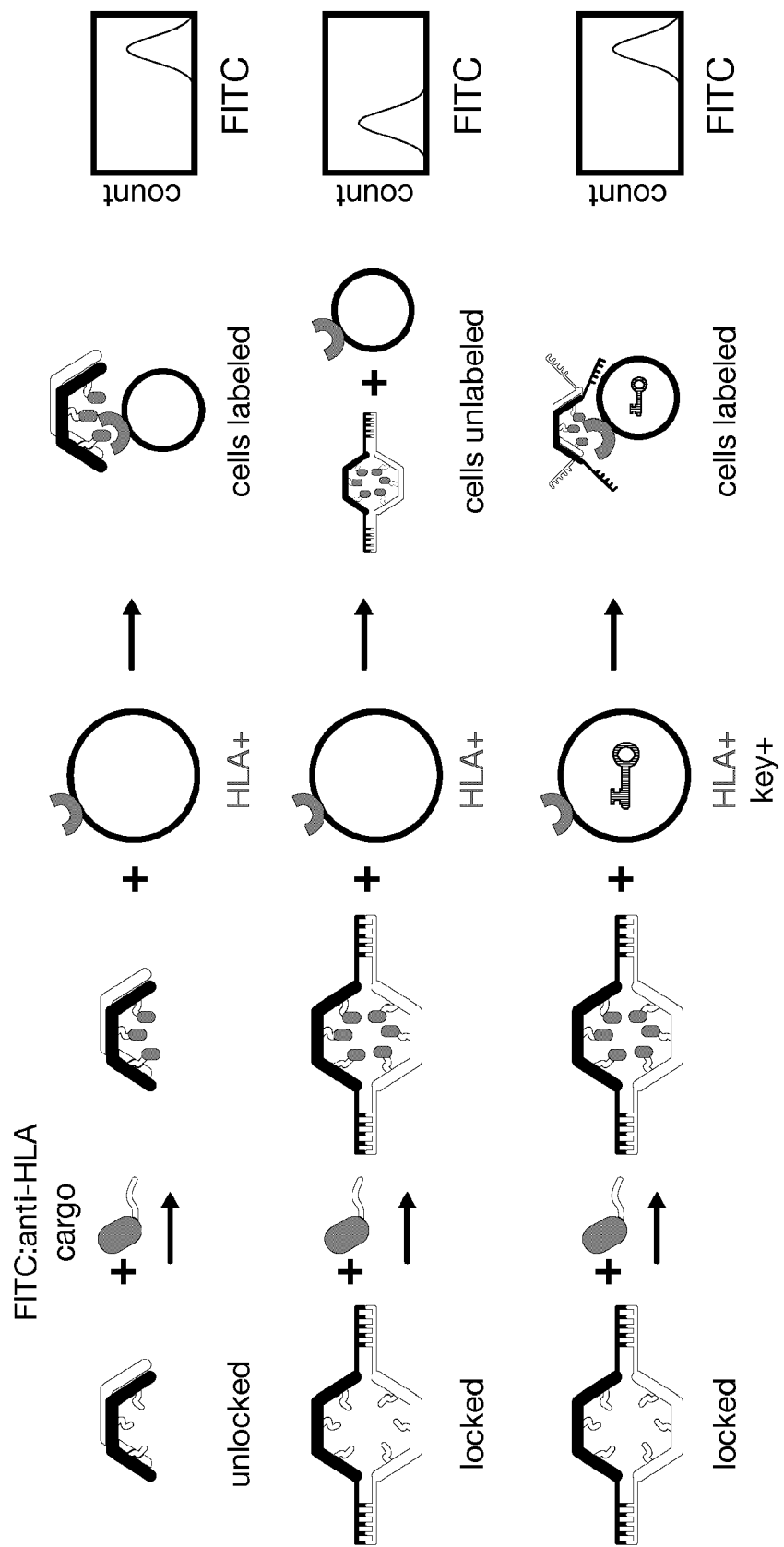
Figure 4B:
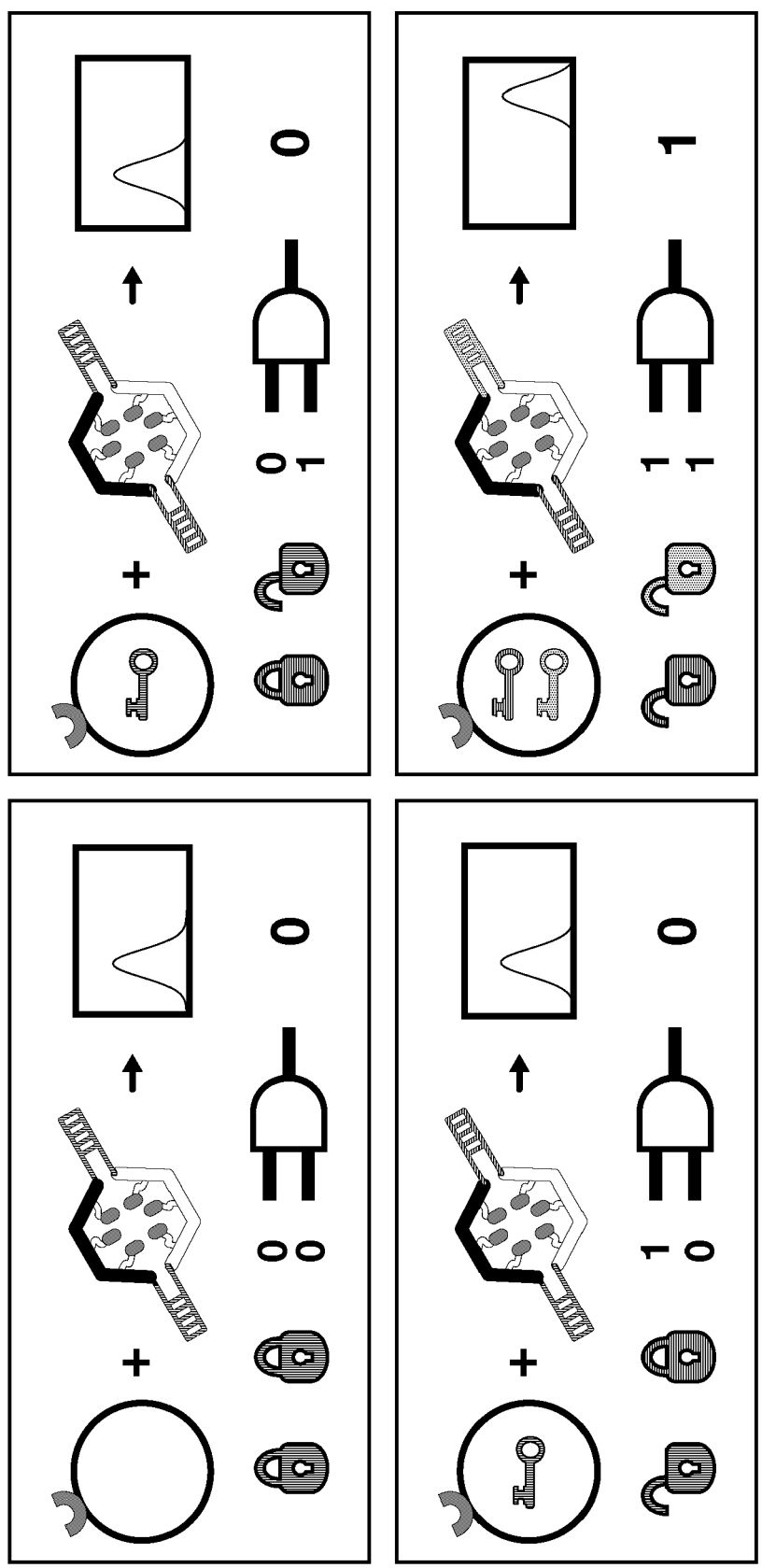
Figure 4C:
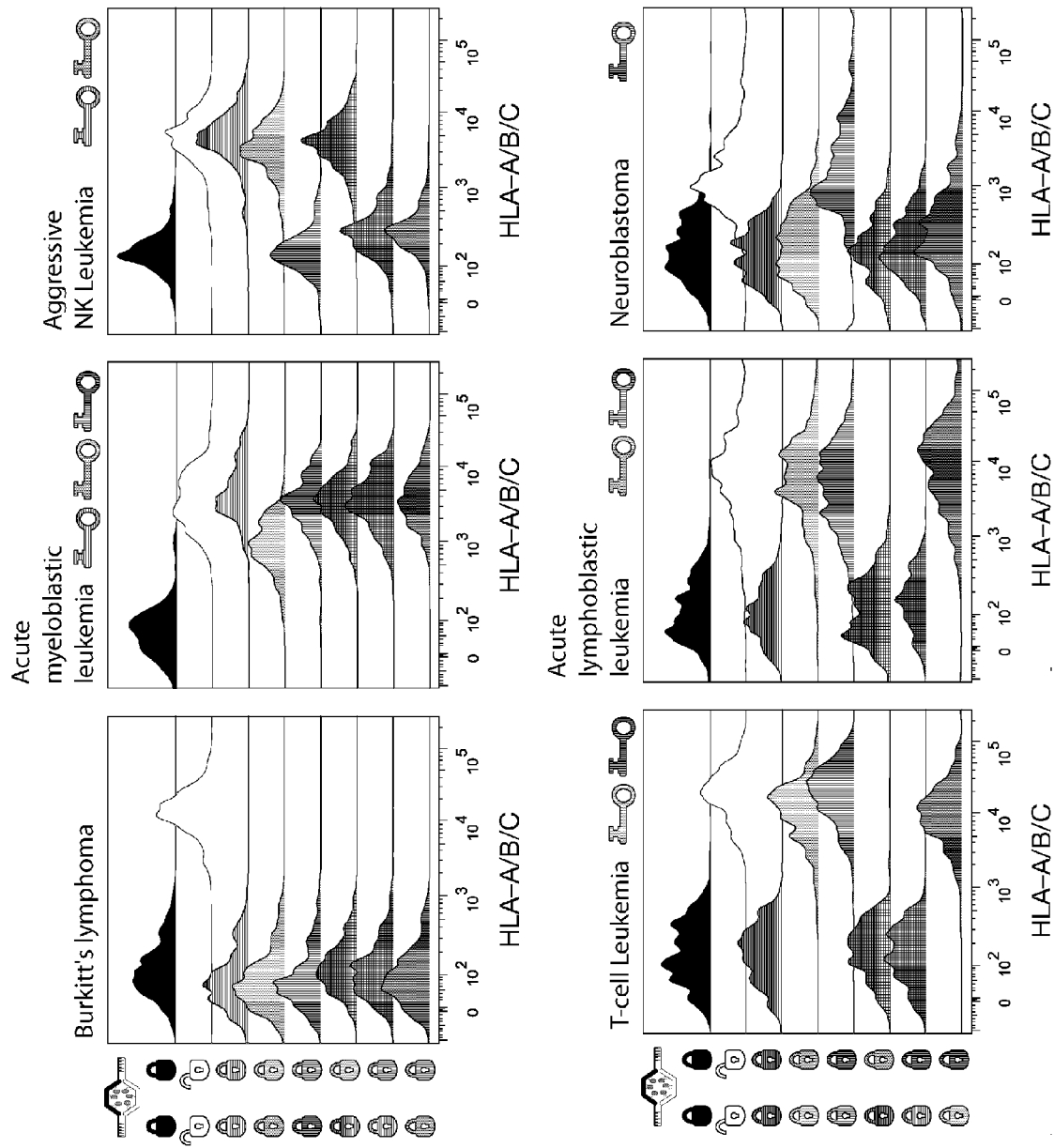

When the input antigen keys do not correspond to the antigen recognized by the aptamer locks, the DNA origami device remains inactive. As depicted in FIG. 4A, FITC-labeled antibody fragments are loaded as payload into DNA origami devices. Unlocked devices readily allow cell binding and result in a significant shift in the histogram peak on flow-cytometry (FIG. 4A, top). When locked devices are mixed with cell types that do not bear the cognate antigen to both aptamer locks, the device remains inactive, sequestering the dye-labeled cargo. When analyzed by flow-cytometry, cells that do not bind active robots only display baseline fluorescence (FIG. 4A, middle). Cells that are able to activate and bind to both aptamers of the DNA origami device display a significant shift in the histogram peak (FIG. 4A, bottom). Thus, the aptamer-encoded locks can be conceptualized as an AND gate responding to molecular inputs expressed by cells (FIG. 4B). As depicted in FIG. 4C, six versions of the robot with different aptamer lock combinations were combined with various cell lines. The contacted cells displayed varying states of activation depending on the cell type and aptamer lock pair.

Figure 4G:
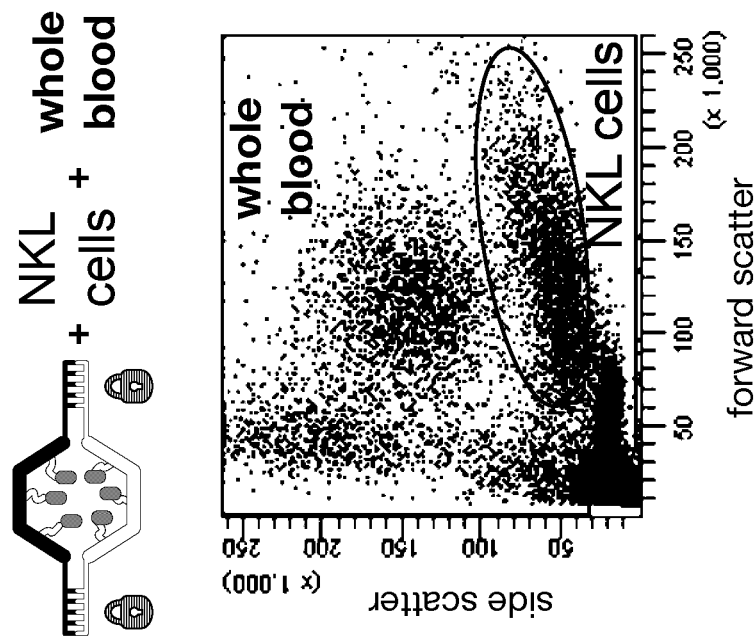
Figure 4F:
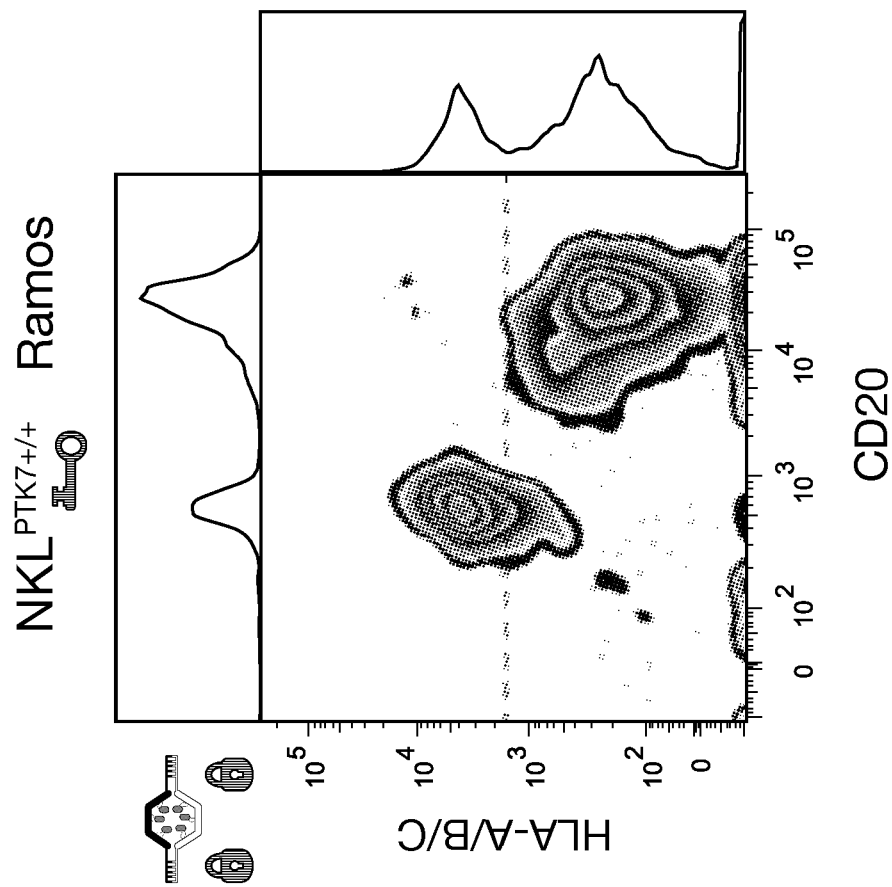

By use of targeted, controlled transport, the DNA origami device can be used to skew cell-cell communication and signaling events. As an example, growth factor signaling was manipulated in a target cell population using monoclonal antibodies as a payload. Monoclonal anti-human CD33 and anti-human CDw328 were selected due to their reported ability to suppress leukemic cell growth. A DNA origami device able to target NKL, a cell line isolated from a patient with aggressive NK cell leukemia was designed and synthesized as described above. NKL cells over-express platelet-derived growth factor (PDGF)-ββ. Thus, the aptamer latch was of the DNA origami device was designed using an aptamer able to bind to PDGF-BB. NKL and Jurkat cells were mixed, labeled with FITC-anti human CD3ε and incubated with devices loaded with APC-anti human HLA A/B/C Fab' for 30 minutes. Devices locked with stabilizing staples did not react with the cell surface molecules, while latching the device with an aptamer latch alone enabled the device to discriminate NKL cells from a mixed population (FIGS. 4D-4F).

To test the ability of the DNA origami devices to distinguish NKL cells from healthy whole blood, the DNA origami device described above was added to a solution containing a mixture of healthy human blood cells and NKL leukemia cells. As depicted in FIG. 4G, the DNA origami devices were able to distinguish NKL cells from healthy whole blood with high precision.

The DNA origami device/cell interface was investigated in two different contexts. First, devices loaded with a combination of anti-human CD33 and anti-human CDw328 Fab' fragments and guided by the same buffer were used to treat NKL cells at various concentrations (FIG. 5A). As depicted in FIGS. 5B-5C, the DNA origami devices suppressed Akt/Protein Kinase B and Jun N-terminal Kinase (JNK) signaling and induced growth arrest in NKL cells in a time- and dose-dependent fashion.

As depicted in the schematics of FIGS. 5D-5E, one possible use of the DNA origami devices is as artificial antigen presenting cells for the activation of T cells. As depicted in FIG. 5F, incubation for 1 hour with devices loaded with anti-human CD3ε Fab' successfully activated Jurkat T cells, as indicated by expression of phosphorylated Syk/ZAP-70 by intracellular flow cytometry. These findings demonstrate that the DNA origami devices can induce a variety of significant and tunable changes in cell behavior and direct it towards a desired outcome.

Example 3

Aptamer-Latch Optimization

Figure 6A:
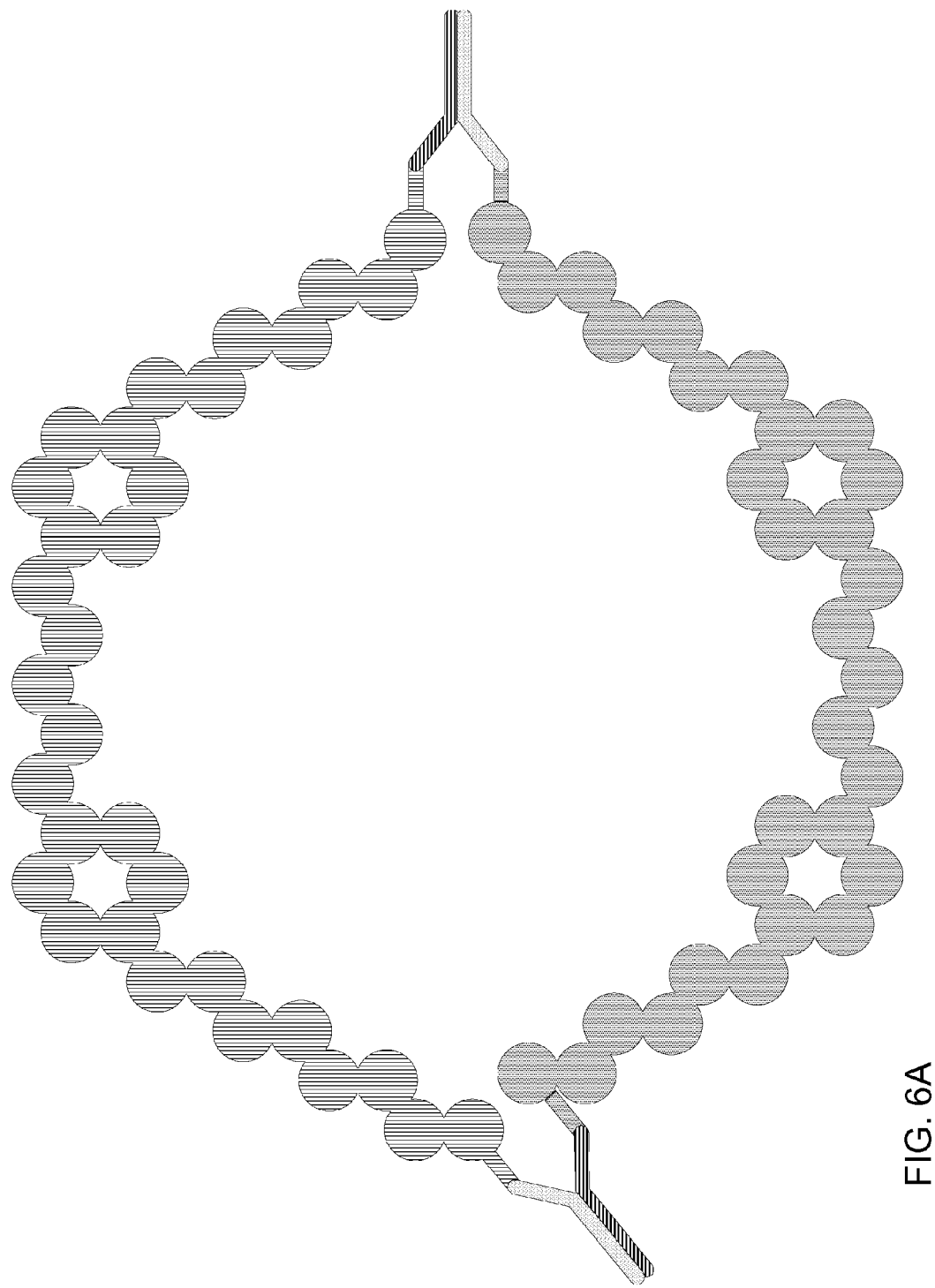
FIG. 6A shows a schematic view of a DNA origami device.
Figure 6B:
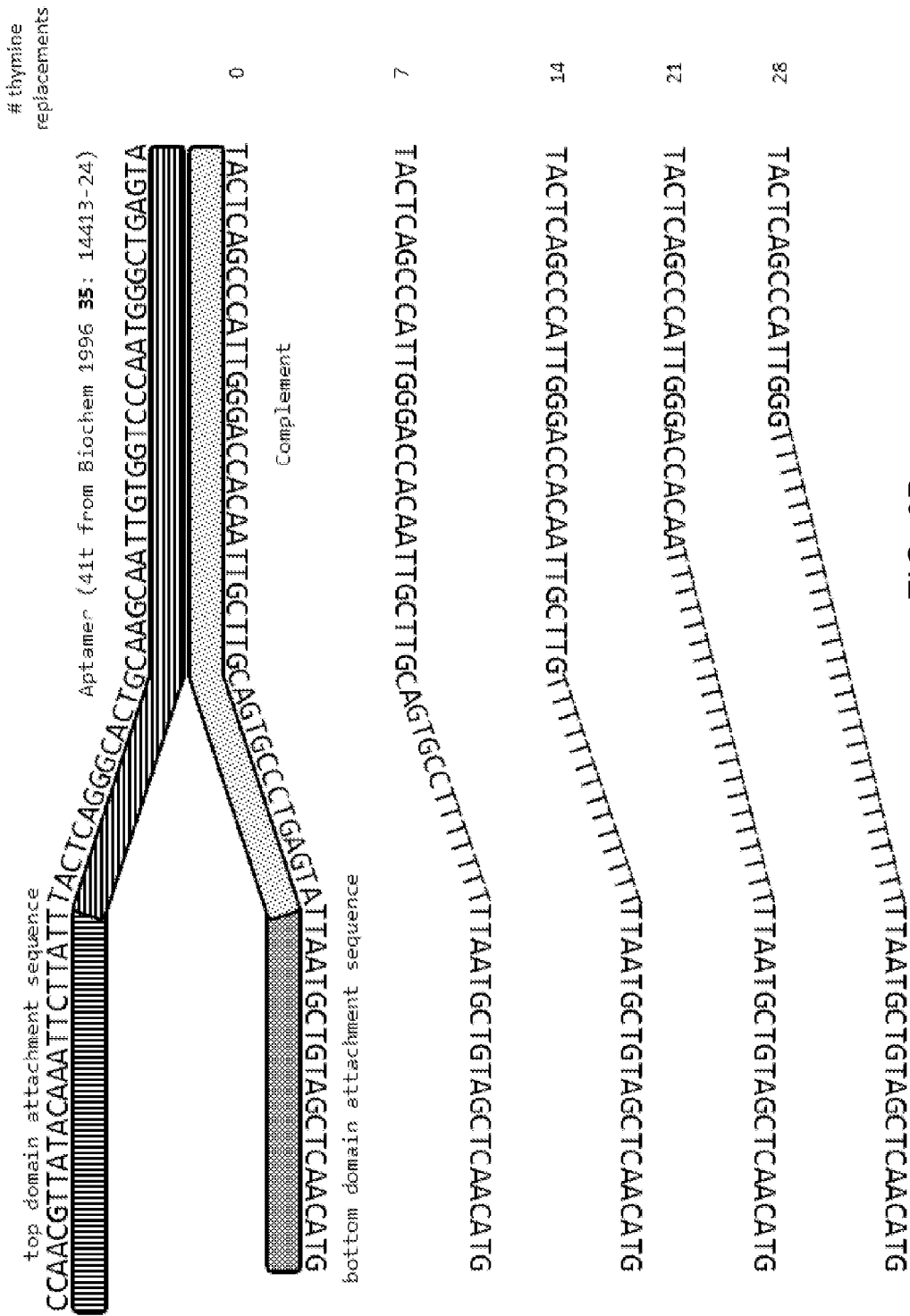
FIG. 6B shows latch sequences (SEQ ID NO:229 through SEQ ID NO:234, respectively, from top to bottom) in which different numbers of latch nucleotides are replaced with thymine.

To determine the effect of aptamer-complement duplex length on DNA origami device function, a series of DNA origami devices having different numbers of mismatches between their aptamer and latch domains were designed and synthesized. To avoid compromising antigen-binding by the aptamer domain, the mismatches were created by varying latch domain sequences by replacing several bases with thymines without changing the sequence of the aptamer domain. Complement strands were designed with 0, 7, 14, 21 and 28 replacement thymine bases. FIG. 6A shows a schematic orthographic view of the devices, in which helices are replaced as circles, along with aptamer based locks (lines). FIG. 6B shows detail of the latch shown on the right side of FIG. 6A, including the sequences of the latch domains and the various complement strands with thymine replacements.

A microbead-based assay coupled with quantitative flow cytometry (qFCM) was performed to determine the rate of opening for the various versions of the DNA origami devices, as well as the probability for a given device to open per unit of time. Cy3-labeled devices were constructed and then loaded with payload oligos modified with 5' BioTEG. Devices that opened in response to aptamer/antigen binding expose their biotinylated payload and are able to label the microbeads, which are then analyzed by qFCM. Acquisition was made at precalibrated photomultiplier tube voltages so that median fluorescence values represent molecular equivalent of soluble fluorochrome (MESF).

Figure 7:
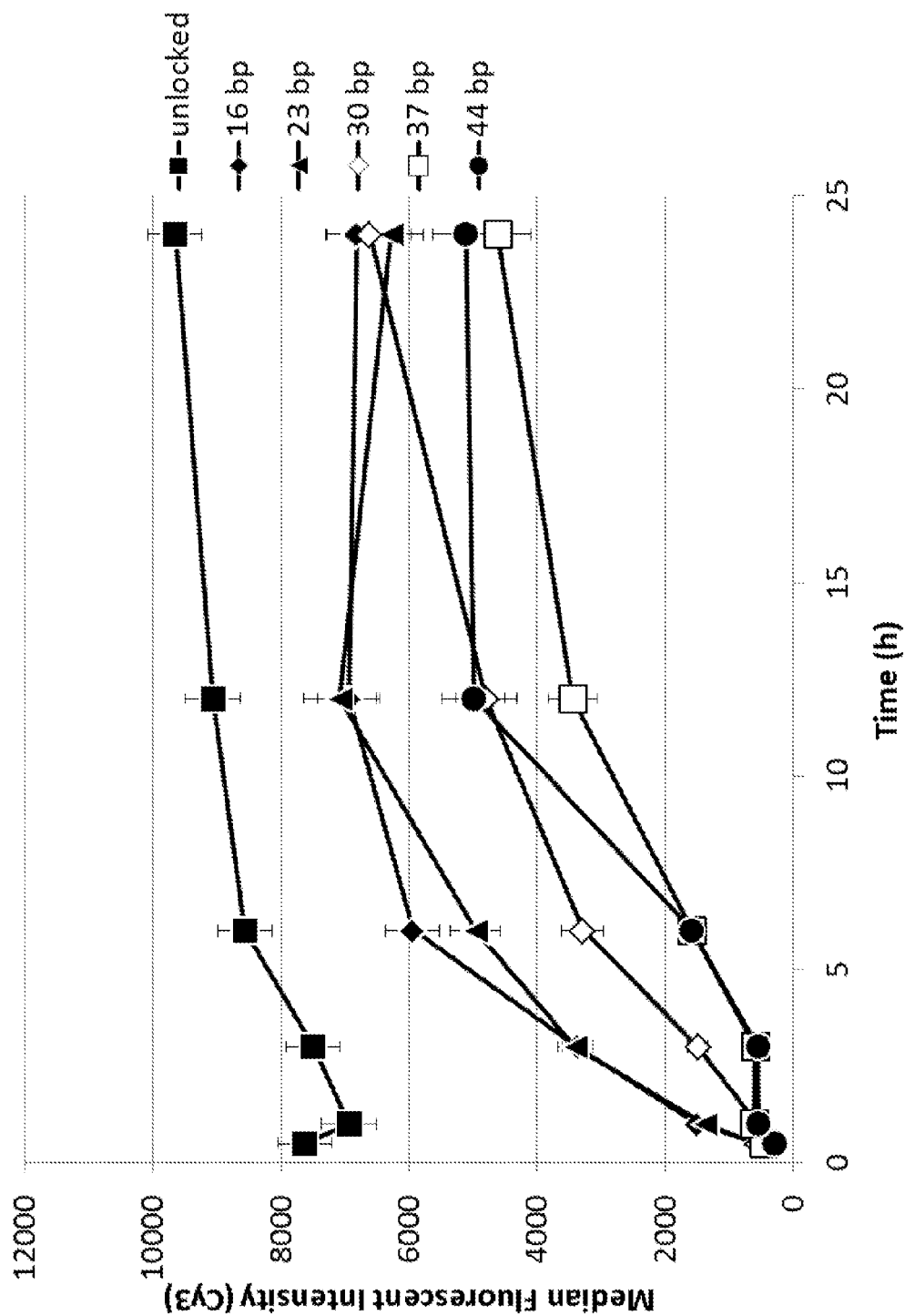
FIG. 7 shows the activation-rate dependence on latch duplex length for exemplary DNA origami devices at an antigen (PDGF) concentration of 10 nM.
Figure 8:
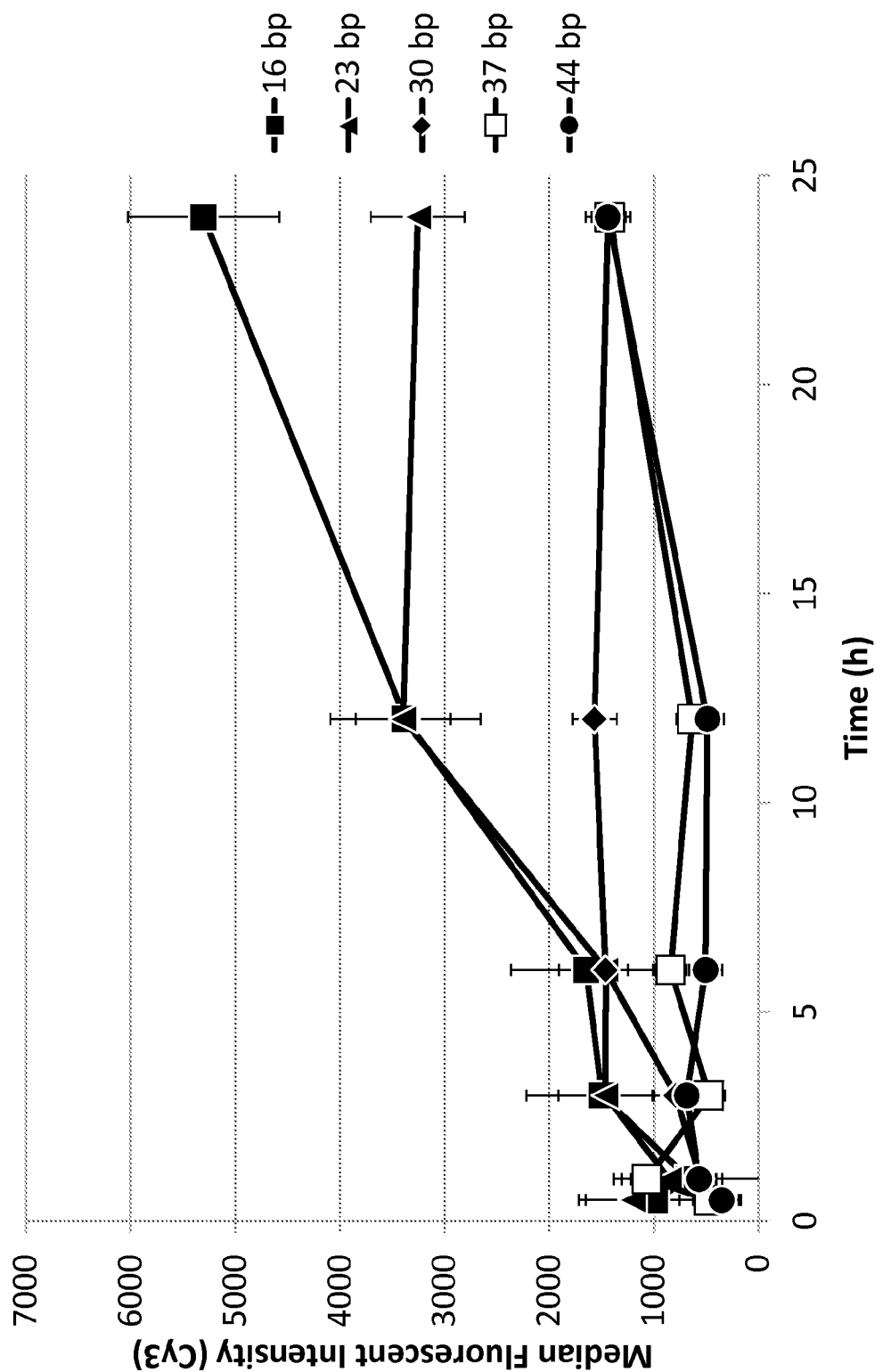
FIG. 8 shows the activation-rate dependence on latch duplex length for exemplary DNA origami devices at an antigen (PDGF) concentration of 0.1 nM.
Figure 9:
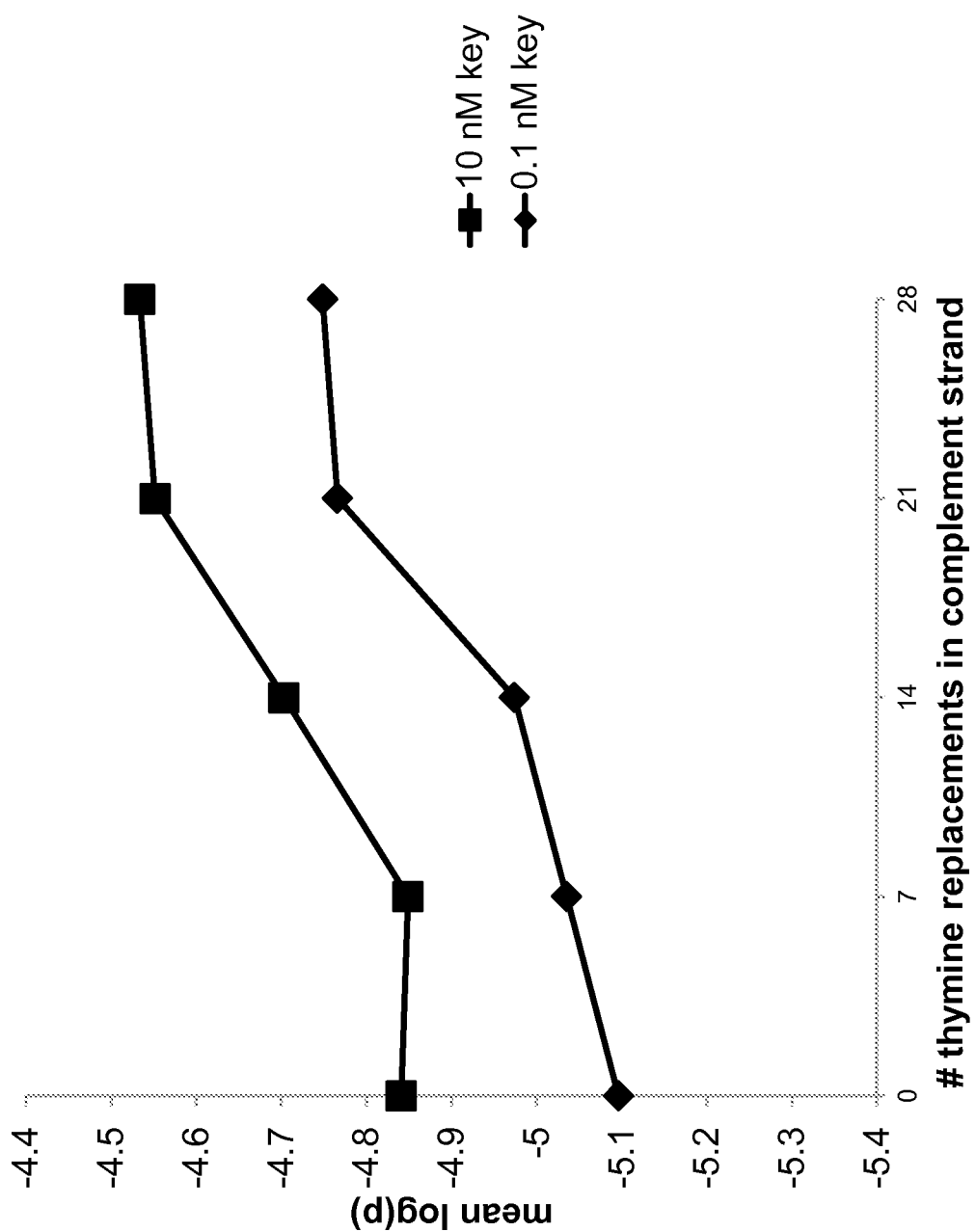
FIG. 9 shows the probability per second (p) that exemplary DNA origami devices having varying latch duplex lengths will open at a given antigen (key) concentration.

The binding of a population of unlocked devices were first measured in order to determine baseline parameters for the assay. Open devices saturated the microbeads after 30 minutes, with a binding capacity of approximately 100,000 devices per microbead. To examine how lock design affected test activation rate, the various device versions were incubated with 10 nM antigen (PDGF) for 24 hours and the fraction of open devices were determined at various time points using the microbead assay. As depicted in FIG. 7, devices with more latch mismatches were able to open faster than those with fewer mismatches. A similar result was obtained when a lower antigen (key) concentration of 0.1 nM was used (FIG. 8). Based on these results, the probability per second (p) that any given device will open was calculated. This value for each device version, expressed as mean log(p), is depicted in FIG. 9.

Figure 10:
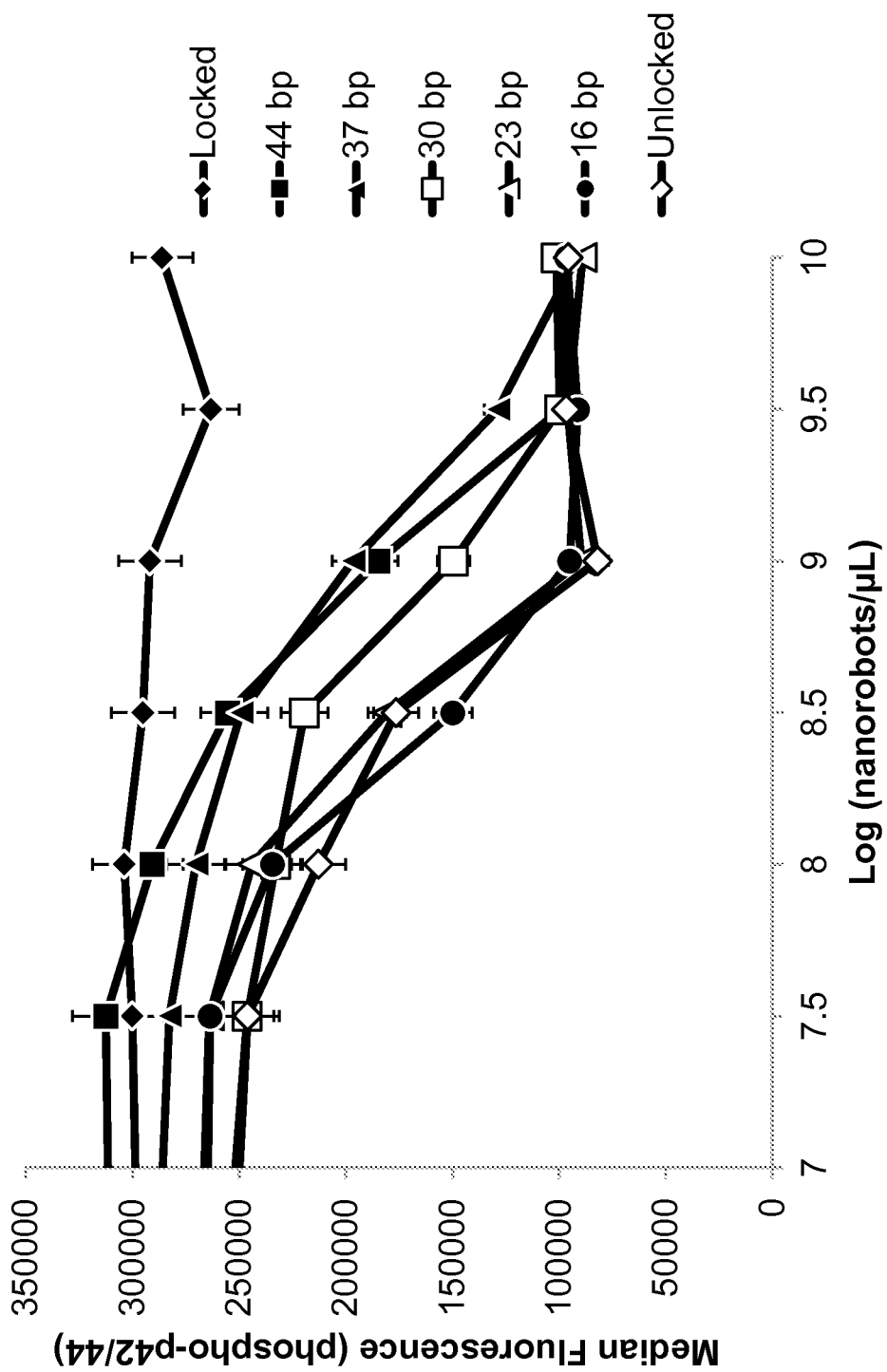
FIG. 10 shows the activation of NK leukemia cells by different concentrations of exemplary DNA origami devices that have varying latch duplex lengths.

A functional assay was performed to determine how the different lock versions affected device function (FIG. 10). Devices with 16, 23, 30, 37 and 34 bp lock duplex lengths were loaded with anti-CD33 and anti-CD232a Fab' antibody fragments and their signaling phosphorylation of the p42/44 kinase ERK was compared. Each device version was tested at varying concentrations (0-10 nM) for its ability to stimulate cell signaling in aggressive NK leukemia cells. Signaling levels were determined by intracellular flow cytometry by measuring phosphorylation levels of the p42/44 kinase ERK. Locks with 0 or 7 thymine replacements exhibited similar profiles (possibly indicating that the first 7 base pairs of the molecular latch are typically unzipped). As depicted in FIG. 10, devices with weaker locks (more mismatches) were able to stimulate cell signaling at lower device concentrations.

Figure 11:
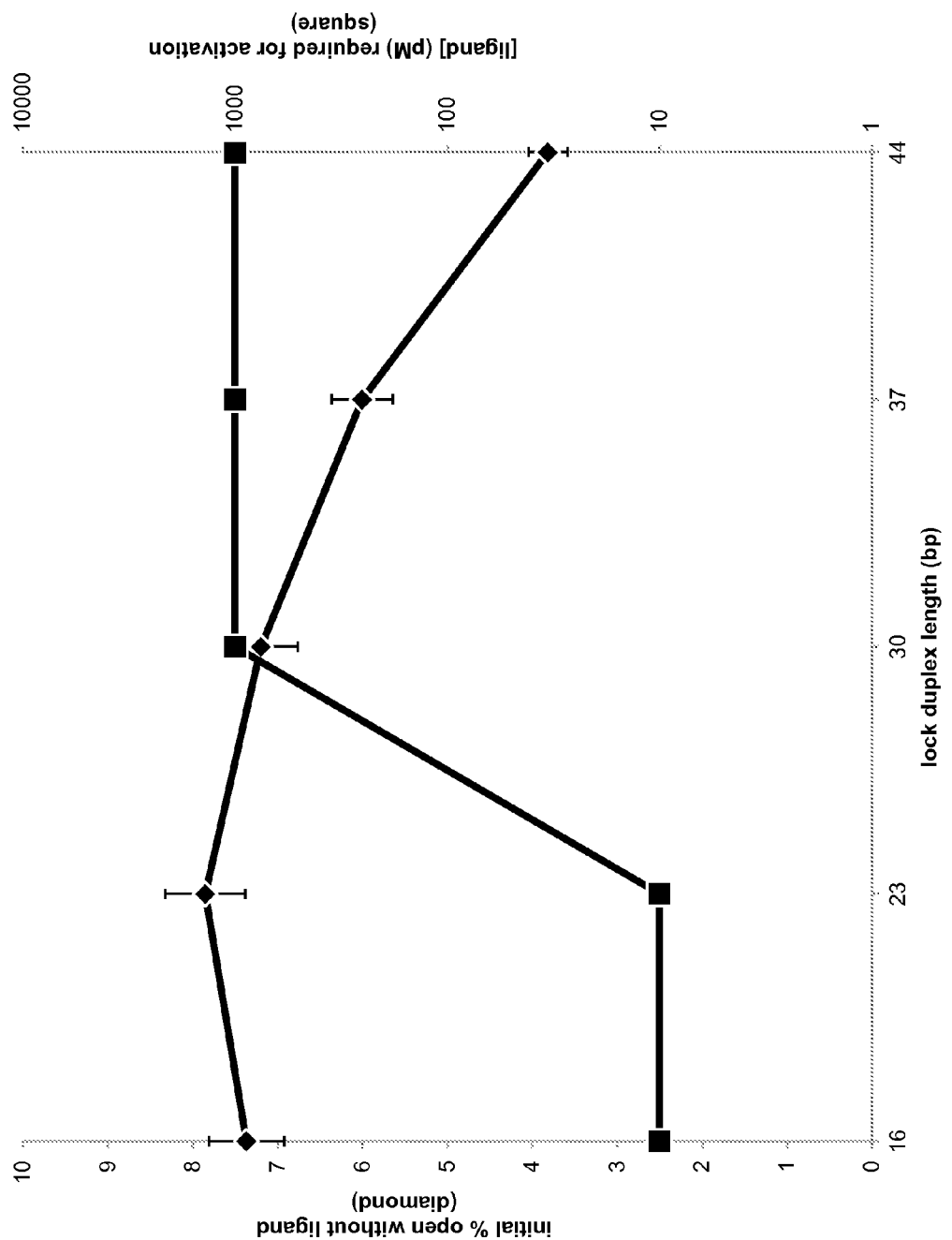
FIG. 11 shows the percentage of exemplary DNA origami devices with different latch (lock) duplex lengths that are open in the absence of activating ligand and the concentration of antigen (ligand) that was required for DNA origami device activation.

In designing a lock system, it may be desirable to balance device sensitivity against device leakiness. Fluorescently labeled devices with anti-PDGF aptamer-latch locks (duplex lengths of 16, 23, 30, 37 and 44 bp) were loaded with biotinylated cargo and incubated with streptavidin-coated beads and then analyzed by flow cytometry. A positive control of 100% open devices was used to establish a baseline fluorescence value, which was used to determine the percentage of each locked device that was initially open. The same device versions were also tested for the minimum concentration of ligand that was required to achieve a measurable activation response. Each version of the device was incubated with streptavidin-coated beads in the presence of increasing concentrations of PDGF, and then tested for activation by flow cytometry. As depicted in FIG. 11, by optimizing the lock strength by introducing mismatches between the aptamer domain and the latch domain, a 100 fold improvement in device sensitivity was achieved by tuning the duplex strength.

Equivalents

Those skilled in the art will recognize, or be able to ascertain using no more than routine experimentation, many equivalents of the specific embodiments of the subject matter described herein. Such equivalents are intended to be encompassed by the following claims.

INCORPORATION BY REFERENCE

All publications, patents, and patent applications cited in this specification are herein incorporated by reference to the same extent as if each individual publication or patent application was specifically and individually indicated to be incorporated by reference.

We claim:

1. A DNA origami device comprising a scaffold strand and a plurality of staple strands,
   - one of the staple strands comprises an aptamer domain capable of binding to an antigen;
   - another of the staple strands comprises a latch domain hybridized to the aptamer domain, the latch domain sequence selected such that the aptamer domain is capable of binding to the antigen such that the antigen displaces the latch domain;
   - the aptamer domain and the latch domain, when hybridized to one another, hold the device in a closed configuration; and
   - the device transitions to an open configuration when the aptamer domain and the latch domain are not hybridized to one another, the DNA origami device has a shape that (a) allows a particle smaller than the inner cross-section of the DNA origami device to access an inner surface of the DNA origami device, and (b) sterically precludes a particle larger than the inner cross-section of the DNA origami device from accessing an inner surface of the device.

2. A DNA origami device comprising a scaffold strand and a plurality of staple strands, wherein:
   - one of the staple strands comprises a first aptamer domain capable of binding to a first antigen;
   - another of the staple strands comprises a second aptamer domain capable of binding to a second antigen;
   - yet another of the staple strands comprises a first latch domain hybridized to the first aptamer domain, the first latch domain sequence selected such that the first aptamer domain is capable of binding to the first antigen such that the first antigen displaces the first latch domain;
   - still another of the staple strands comprises a second latch domain hybridized to the second aptamer domain, the second latch domain sequence selected such that the second aptamer domain is capable of binding to the second antigen with a greater affinity than it is capable of binding to the second latch domain;
   - the first aptamer domain hybridized to the first latch domain, and the second aptamer domain hybridized to the second latch domain, hold the device in a closed configuration; and
   - the device transitions to an open configuration when the first aptamer domain is not hybridized to the first latch domain and the second aptamer domain is not hybridized to the second latch domain, the DNA origami device has a shape that (a) allows a particle smaller than the inner cross-section of the DNA origami device to access an inner surface of the DNA origami device, and (b) sterically precludes a particle larger than the inner cross-section of the DNA origami device from accessing an inner surface of the device.

3. The DNA origami device of claim 1, wherein the device is biased to the open configuration.

4. The DNA origami device of claim 1, wherein one of the staple strands comprises a handle domain capable of binding to a moiety.

5. The DNA origami device of claim 4, wherein multiple staple strands comprise a handle domain capable of binding a plurality of moieties at a stoichiometrically predetermined ratio.

6. The DNA origami device of claim 4, wherein the plurality of staple strands are selected such that:
   - a moiety bound by the handle domain is positioned on an inner surface of the DNA origami device when the device is in the closed configuration; and the transition to the open configuration causes a moiety bound by the handle domain to be positioned on an outer surface of the DNA origami device.

7. The DNA origami device of claim 6, wherein the handle domain is bound to a moiety.

8. The DNA origami device of claim 7, wherein the moiety comprises a linker oligonucleotide having a sequence complementary to the sequence of the handle domain, and wherein the moiety is bound to the handle domain through the hybridization of the linker oligonucleotide to the handle domain.

9. The DNA origami device of claim 7, wherein the moiety comprises at least one of: an antibody, an antibody fragment, a cell surface receptor ligand, a biologically active fragment of a cell surface receptor ligand, a small molecule, a nucleic acid, a DNAzyme, an aptamer, a lipid, a glycan, a glycoprotein, a glycolipid, a proteoglycan, a nanoparticle, a quantum dot, a fluorophore, and a nanocrystal.

10. The DNA origami device of claim 6, wherein one of the staple strands comprises a second handle domain capable of binding to a second moiety, wherein staple strands are selected such that:
a moiety bound by the second handle domain is positioned on an inner surface of the DNA origami device when the device is in the closed configuration; and
the transition to the open configuration causes a moiety bound by the second handle domain to be positioned on an outer surface of the DNA origami device.

11. The DNA origami device of claim 6, wherein at least one antigen is a cancer cell-specific antigen.

12. The DNA origami device of claim 1, wherein staple strands are selected such that the DNA origami device comprises a first domain and a second domain, wherein a first end of the first domain is attached to a first end of the second domain by at least one single-stranded DNA hinge and the second end of the first domain is attached to the second end of the second domain by the hybridization of the aptamer domain to the latch domain.

13. The DNA origami device of claim 12, wherein staple strands are selected such that the second end of the first domain becomes unattached to the second end of the second domain if the aptamer domain is contacted by a respective antigen.

14. The DNA origami device of claim 2, wherein the first antigen and the second antigen are different from one another.

15. A DNA origami device comprising a scaffold strand and a plurality of staple strands, wherein:
one of the staple strands comprises a handle domain bound to a moiety; and
staple strands are selected such that:
the DNA origami device has a shape that (a) allows a particle smaller than the inner cross-section of the DNA origami device to access an inner surface of the DNA origami device, and (b) sterically precludes a particle larger than the inner cross-section of the DNA origami device from accessing the inner surface; and
the moiety bound by the handle domain is positioned on the inner surface.

16. A method of delivering a moiety to a cell expressing an antigen, comprising contacting the cell with the DNA origami device of claim 1 carrying the moiety, thereby allowing the antigen to displace the latch domain from the aptamer domain, causing the device to transition to the open configuration, and allowing the moiety to contact the cell.

17. A method of sequestering a particle smaller than the inner cross-section of the DNA origami device in size, comprising contacting the particle with a DNA origami device of claim 1 carrying a moiety, wherein the moiety is capable of specifically binding to the particle.

18. The method of claim 17, further comprising delivering the sequestered particle to a cell expressing an antigen, comprising contacting the cell with the DNA origami device in which the particle has been sequestered, thereby allowing the antigen to displace the latch domain from the aptamer domain, causing the device to transition to the open configuration and allowing the particle to contact the cell.

19. A DNA origami device comprising a scaffold strand and a plurality of staple strands,
one of the staple strands comprises an aptamer domain capable of binding to an antigen;
another of the staple strands comprises a latch domain hybridized to the aptamer domain, the latch domain sequence selected such that the aptamer domain is capable of binding to the antigen such that the antigen displaces the latch domain;
the aptamer domain and the latch domain, when hybridized to one another, hold the device in a closed configuration; and
the device transitions to an open configuration when the aptamer domain and the latch domain are not hybridized to one another,
wherein the plurality of staple strands are selected such that: one of the staple strands comprises a handle domain, wherein
a moiety bound by the handle domain is positioned on an inner surface of the DNA origami device when the device is in the closed configuration; and
the transition to the open configuration causes a moiety bound by the handle domain to be positioned on an outer surface of the DNA origami device.

20. The DNA origami device of claim 19, wherein the moiety comprises a linker oligonucleotide having a sequence complementary to the sequence of the handle domain, and wherein the moiety is bound to the handle domain through the hybridization of the linker oligonucleotide to the handle domain.

21. The DNA origami device of claim 19, wherein the moiety comprises at least one of: an antibody, an antibody fragment, a cell surface receptor ligand, a biologically active fragment of a cell surface receptor ligand, a small molecule, a nucleic acid, a DNAzyme, an aptamer, a lipid, a glycan, a glycoprotein, a glycolipid, a proteoglycan, a nanoparticle, a quantum dot, a fluorophore, and a nanocrystal.

22. The DNA origami device of claim 19, wherein one of the staple strands comprises a second handle domain capable of binding to a second moiety, wherein staple strands are selected such that:
a moiety bound by the second handle domain is positioned on an inner surface of the DNA origami device when the device is in the closed configuration; and
the transition to the open configuration causes a moiety bound by the second handle domain to be positioned on an outer surface of the DNA origami device.

23. The DNA origami device of claim 19, wherein the antigen is a cancer cell-specific antigen.

24. A DNA origami device comprising a scaffold strand and a plurality of staple strands, one of the staple strands comprises an aptamer domain capable of binding to an antigen;
another of the staple strands comprises a latch domain hybridized to the aptamer domain, the latch domain sequence selected such that the aptamer domain is capable of binding to the antigen such that the antigen displaces the latch domain;

the aptamer domain and the latch domain, when hybridized to one another, hold the device in a closed configuration; and the device transitions to an open configuration when the aptamer domain and the latch domain are not hybridized to one another, and wherein the DNA origami device further includes a locking staple having a single-stranded toehold domain, wherein the locking staple is selected such that the presence of the locking staple on the DNA origami device prevents transition to the open configuration; and contacting the locking staple with an oligonucleotide having a complementary sequence displaces the locking staple from the DNA origami device.

* * * * *